US010905650B2

(12) United States Patent
Fernandez et al.

(10) Patent No.: US 10,905,650 B2
(45) Date of Patent: Feb. 2, 2021

(54) GUMMY COMPOSITIONS FOR NUTRITIONAL SUPPLEMENTATION

(71) Applicant: Exeltis USA, Inc., Florham Park, NJ (US)

(72) Inventors: Eduardo Fernandez, Hoboken, NJ (US); Charles Balzer, Chatham, NJ (US)

(73) Assignee: Exeltis USA, Inc., Chatham, NJ (US)

( * ) Notice: Subject to any disclaimer, the term of this patent is extended or adjusted under 35 U.S.C. 154(b) by 55 days.

(21) Appl. No.: 14/792,452

(22) Filed: Jul. 6, 2015

(65) Prior Publication Data

US 2015/0306029 A1 Oct. 29, 2015

Related U.S. Application Data

(63) Continuation-in-part of application No. 14/214,476, filed on Mar. 14, 2014, now abandoned.

(60) Provisional application No. 61/800,088, filed on Mar. 15, 2013.

(51) Int. Cl.
| | |
|---|---|
| *A61K 9/00* | (2006.01) |
| *A61K 31/07* | (2006.01) |
| *A61K 31/4415* | (2006.01) |
| *A61K 31/714* | (2006.01) |
| *A61K 31/375* | (2006.01) |
| *A61K 31/593* | (2006.01) |
| *A61K 31/355* | (2006.01) |
| *A61K 31/455* | (2006.01) |
| *A61K 33/18* | (2006.01) |
| *A61K 31/133* | (2006.01) |
| *A61K 33/26* | (2006.01) |
| *A61K 31/202* | (2006.01) |
| *A61K 31/194* | (2006.01) |
| *A61K 31/519* | (2006.01) |
| *A61K 31/14* | (2006.01) |
| *A61K 31/59* | (2006.01) |
| *A61K 31/215* | (2006.01) |
| *A23G 3/36* | (2006.01) |
| *A23L 33/00* | (2016.01) |
| *A23L 33/15* | (2016.01) |
| *A23L 33/16* | (2016.01) |

(52) U.S. Cl.
CPC ............ *A61K 9/0056* (2013.01); *A23G 3/364* (2013.01); *A23G 3/368* (2013.01); *A23L 33/15* (2016.08); *A23L 33/16* (2016.08); *A23L 33/40* (2016.08); *A61K 31/07* (2013.01); *A61K 31/133* (2013.01); *A61K 31/14* (2013.01); *A61K 31/194* (2013.01); *A61K 31/202* (2013.01); *A61K 31/215* (2013.01); *A61K 31/355* (2013.01); *A61K 31/375* (2013.01); *A61K 31/4415* (2013.01); *A61K 31/455* (2013.01); *A61K 31/519* (2013.01); *A61K 31/59* (2013.01); *A61K 31/593* (2013.01); *A61K 31/714* (2013.01); *A61K 33/18* (2013.01); *A61K 33/26* (2013.01); *A23V 2002/00* (2013.01)

(58) Field of Classification Search
USPC ........................................... 426/72
See application file for complete search history.

(56) References Cited

U.S. PATENT DOCUMENTS

2007/0196447 A1* 8/2007 Weg ..................... A61K 9/0053
424/440
2010/0099640 A1* 4/2010 Geuns .................... C07H 15/18
514/34

OTHER PUBLICATIONS

Cox: Prenatal nutrition: special considerations; Minerva Ginecol. Oct. 2009;61(5):373-400.*
Spring Valley: published online at least by Mar. 5, 2012, at: http://web.archive.org/web/20100305172751/http://www.amazon.com/Spring-Valley-Prenatal-Multivitamin-Multimineral/dp/B001QRRI88.*
Zimmermann: Encapsulation of Iron and Other Micronutrients for Food Fortification; Chapter 7: Encapsulation Technologies for Active Food Ingredients and Food Processing; pp. 187-209; Date: Sep. 18, 2009.*
Kaushik: Application of Electrohydrodynamic Technology for Folic Acid Encapsulation; Received: Dec. 9, 2011 / Accepted: Mar. 27, 2012 / Published online: Apr. 26, 2012.*
Spring Valley: http://web.archive.org/web/20100305172751/http://www.amazon.com/Spring-Valley-Prenatal-Multivitamin-Multimineral/dp/B001QRRI88; published at least by Mar. 5, 2010.*
Madziva: Alginate-pectin microcapsules as a potential for folic acid delivery in foods; J Microencapsul. Jun. 2005;22(4):343-51.*
WM: Wellness Mama: Homemade Chewable Vitamins; online at least by Oct. 25, 2012 at http://web.archive.org/web/20121025002314/http://wellnessmama.com/6357/chewable-vitamins.*
Vitafusion: Vitafusion Prenatal, Gummy Vitamins, 90 Count; online at least by May 6, 2010 (as evidenced by the review by D. Won) at: https://www.amazon.com/Vitafusion-Prenatal-Gummy-Vitamins-Count/product-reviews/B003IP8BC8/ref=cm_cr_getr_d_paging_btm_96?ie=UTF8&showViewpoints=1&sortBy=recent&pageNumber=96.*
Laskowski: Homemade gummy vitamins; published online on Mon, Jan. 14, 2013 at: http://www.justapinch.com/recipes/non-edibile/beauty-recipe/homemade-gummy-vitamins.html.*

(Continued)

Primary Examiner — Patricia A George
(74) Attorney, Agent, or Firm — Sheppard Mullin Richter & Hampton LLP

(57) ABSTRACT

Gummy dosage forms comprising gummy compositions for nutritional supplementation, methods for providing nutritional supplementation, and kits comprising gummy compositions for nutritional supplementation are disclosed. Such gummy compositions for nutritional supplementation may provide improved patient compliance relative to non-gummy compositions for nutritional supplementation. These gummy compositions can be used to administer one or more vitamins, minerals, or trace elements.

17 Claims, No Drawings

(56) References Cited

OTHER PUBLICATIONS

Blake: How to Make Your Own Supplements; BM 101; online by Nov. 22, 2011 as verified by: http://web.archive.org/web/20111122001329/http://www.building-muscle101.com/how-to-make-your-own-supplements.html.*

Enfield: ISO: A high-quality multivitamin my kids will actually eat!; published on Mar. 8, 2011 at Delicious Living (see comments on Mar. 9, 2011): http://deliciousliving.com/blog/iso-high-quality-multivitamin-my-kids-will-actually-eat (Year: 2011).*

OSU: Other Nutrients;published online at least Apr. 15, 2003; http://web.archive.org/web/20030212085535/http://lpi.oregonstate.edu/ infocenter/othernuts.html. (Year: 2003).*

DRI: Dietary Reference Intakes for Thiamin, Riboflavin, Niacin, Vitamin B6, Folate, Vitamin B12, Pantothenic Acid, Biotin, and Choline; published 1998. (Year: 1998).*

IMC: Integrative Medicine Communications: Syrian Clinic: Vitamin B9 (Folic Acid); http://www.syrianclinic.com/med/en/ProfSupplements/VitaminB9FolicAcidps.html; copyright 2000. (Year: 2000).*

Blake: How to Make Your Own Supplements; BM 101; online by Nov. 22, 2011 as verified by: http://web.archive.org/web/20111122001329/http://www.building-muscle101.com/how-to-make-your-own-supplements.html (Year: 2011).*

Coletta: Omega-3 Fatty Acids and Pregnancy; Rev Obstet Gynecol. Fall 2010; 3(4): 163-171. (Year: 2010).*

\* cited by examiner

GUMMY COMPOSITIONS FOR NUTRITIONAL SUPPLEMENTATION

CROSS-REFERENCE TO RELATED APPLICATION

This is a continuation-in-part of nonprovisional patent application Ser. No. 14/214,476, filed Mar. 14, 2014, which claims the benefit under 35 U.S.C. § 119(e) of U.S. Provisional Patent Application Ser. No. 61/800,088, filed on Mar. 15, 2013, the contents of which are hereby expressly incorporated by reference in their entirety.

FIELD OF THE INVENTION

The present invention relates to gummy dosage forms comprising various gummy compositions for nutritional supplementation, methods of administration of various gummy compositions for nutritional supplementation, and kits comprising various gummy compositions for nutritional supplementation.

BACKGROUND OF THE INVENTION

Supplemental iron is extremely important during pregnancy due to the large increase in blood plasma volume and erythropoetic (red blood cell production) activity. Anemia is common in pregnancy, notably in the absence of supplemental iron consumption. Negative outcomes of pregnancy have been correlated with an iron-specific anemic state during pregnancy.

Docosahexaenoic acid ("DHA") is a primary structural component of the human brain, cerebral cortex, skin, sperm, testicles, and retina. Studies indicate that women, on average, consume less DHA than the recommended daily intake. Fish is a primary source of dietary DHA. Thus, the decreased intake may be due to a moderate avoidance of dietary seafood secondary to fear of seaborne contaminants (e.g., mercury and polychlorinated biphenyls).

Iodine plays an important role in fetal brain and cognitive development. Studies have demonstrated moderately low systemic levels of iodine in women of childbearing age. Like DHA, low iodine may be due to a general decrease in seafood secondary for fear of seaborne contaminants.

Vitamin D has been shown to have positive effects on the immune system, including during pregnancy. However, epidemiologic studies have demonstrated that a large percentage of pregnant women, including those of childbearing age, possess systemically insufficient levels of vitamin D.

Patient compliance is a problem with current commercially available nutritional supplements, including prenatal vitamins. For example, problems with compliance are sometimes seen when pregnant women have a condition that does not allow them to easily take current commercially available prenatal vitamins, including morning sickness or nausea and vomiting of pregnancy. These conditions may be associated with the iron content in current commercially available prenatal vitamins.

Accordingly, a need exists for compositions that provide suitable nutritional supplementation and that have satisfactory patient compliance. Such compositions may be used, for example, before and during pregnancy.

SUMMARY OF THE INVENTION

Disclosed herein are gummy dosage forms comprising gummy compositions for nutritional supplementation, methods for providing nutritional supplementation to a patient by administering at least one gummy composition, and kits comprising gummy compositions as disclosed herein. In some embodiments, the gummy compositions for nutritional supplementation may provide improved patient compliance relative to non-gummy compositions for nutritional supplementation. In some embodiments, the gummy compositions for nutritional supplementation can be used to administer one or more vitamins, minerals, or trace elements. In certain embodiments, the gummy compositions for nutritional supplementation may comprise iron. In some embodiments, the gummy compositions may be prenatal vitamins. In some embodiments, the gummy compositions may be prenatal vitamins that comprise iron.

Some embodiments herein may provide for methods for providing nutritional supplementation to a patient. The methods may comprise administering at least one gummy composition to the patient, wherein the at least one gummy composition may comprise vitamin A, vitamin $B_6$, vitamin $B_{12}$, vitamin $B_9$, vitamin C, vitamin D, vitamin E, vitamin $B_3$, iodine, choline, iron, and at least one omega-3 fatty acid.

In some embodiments, the methods may comprise administering at least one gummy composition to the patient, wherein at least one gummy composition may comprise a total dosing amount of vitamin A ranging from about 550 IU to about 1650 IU, a total dosing amount of vitamin $B_6$ ranging from about 1 mg to about 4 mg, a total dosing amount of vitamin $B_{12}$ ranging from about 4 µg to about 12 µg, a total dosing amount of vitamin $B_9$ ranging from about 0.5 mg to about 1.5 mg, a total dosing amount of vitamin C ranging from about 10 mg to about 40 mg, a total dosing amount of vitamin D amount ranging from about 500 IU to about 1500 IU, a total dosing amount of vitamin E ranging from about 7.5 IU to about 22.5 IU, a total dosing amount of vitamin $B_3$ ranging from about 7 mg to about 23 mg, a total dosing amount of iodine ranging from about 75 µg to about 225 µg, a total dosing amount of choline ranging from about 5 mg to about 15 mg, a total dosing amount of iron ranging from about 1 mg to about 20 mg, and a total dosing amount of at least one omega-3 fatty acid ranging from about 50 mg to about 150 mg.

In some embodiments, the methods may comprise administering at least one gummy composition to the patient, wherein the at least one gummy composition may comprise a total dosing amount of about 1100 IU vitamin A, a total dosing amount of about 2.5 mg vitamin $B_6$, a total dosing amount of about 8 µg vitamin $B_{12}$, a total dosing amount of about 1 mg vitamin $B_9$, a total dosing amount of about 30 mg vitamin C, a total dosing amount of about 1000 IU vitamin D, a total dosing amount of about 15 IU vitamin E, a total dosing amount of about 15 mg vitamin $B_3$, a total dosing amount of about 150 µg iodine, a total dosing amount of about 10 mg choline, a total dosing amount of about 10 mg iron, and a total dosing amount of about 75 mg omega-3 fatty acid.

In some embodiments, the methods may comprise administering at least one gummy composition to the patient, wherein the at least one gummy composition may comprise a total dosing amount of about 1100 IU vitamin A, a total dosing amount of about 2.5 mg vitamin $B_6$, a total dosing amount of about 8 µg vitamin $B_{12}$, a total dosing amount of about 1 mg vitamin $B_9$, a total dosing amount of about 30 mg vitamin C, a total dosing amount of about 1000 IU vitamin D, a total dosing amount of about 15 IU vitamin E, a total dosing amount of about 15 mg vitamin $B_3$, a total dosing amount of about 150 µg iodine, a total dosing amount of about 10 mg choline, a total dosing amount of about 12 mg iron, and a total dosing amount of about 75 mg omega-3 fatty acid.

In some embodiments, the methods may comprise administering at least one gummy composition to the patient, wherein the at least one gummy composition may comprise a total dosing amount of about 1100 IU vitamin A, a total dosing amount of about 2.5 mg vitamin $B_6$, a total dosing amount of about 8 µg vitamin $B_{12}$, a total dosing amount of about 1 mg vitamin $B_9$, a total dosing amount of about 30 mg vitamin C, a total dosing amount of about 1000 IU vitamin D, a total dosing amount of about 15 IU vitamin E, a total dosing amount of about 15 mg vitamin $B_3$, a total dosing amount of about 150 µg iodine, a total dosing amount of about 10 mg choline, a total dosing amount of about 15 mg iron, and a total dosing amount of about 75 mg omega-3 fatty acid.

In some embodiments, the methods may comprise administering at least one gummy composition to the patient, wherein the at least one gummy composition may comprise a total dosing amount of at least about 1100 IU vitamin A, a total dosing amount of at least about 2.5 mg vitamin $B_6$, a total dosing amount of at least about 8 µg vitamin $B_{12}$, a total dosing amount of at least about 1 mg vitamin $B_9$, a total dosing amount of at least about 30 mg vitamin C, a total dosing amount of at least about 1000 IU vitamin D, a total dosing amount of at least about 15 IU vitamin E, a total dosing amount of at least about 15 mg vitamin $B_3$, a total dosing amount of at least about 150 µg iodine, a total dosing amount of at least about 10 mg choline, a total dosing amount of at least about 10 mg iron, and a total dosing amount of at least about 75 mg omega-3 fatty acid.

In some embodiments, the methods may comprise administering at least one gummy composition to the patient, wherein the at least one gummy composition may comprise a total dosing amount of at least about 1100 IU vitamin A, a total dosing amount of at least about 2.5 mg vitamin $B_6$, a total dosing amount of at least about 8 µg vitamin $B_{12}$, a total dosing amount of at least about 1 mg vitamin $B_9$, a total dosing amount of at least about 30 mg vitamin C, a total dosing amount of at least about 1000 IU vitamin D, a total dosing amount of at least about 15 IU vitamin E, a total dosing amount of at least about 15 mg vitamin $B_3$, a total dosing amount of at least about 150 µg iodine, a total dosing amount of at least about 10 mg choline, a total dosing amount of at least about 12 mg iron, and a total dosing amount of at least about 75 mg omega-3 fatty acid.

In some embodiments, the methods may comprise administering at least one gummy composition to the patient, wherein the at least one gummy composition may comprise a total dosing amount of at least about 1100 IU vitamin A, a total dosing amount of at least about 2.5 mg vitamin $B_6$, a total dosing amount of at least about 8 µvitamin $B_{12}$, a total dosing amount of at least about 1 mg vitamin $B_9$, a total dosing amount of at least about 30 mg vitamin C, a total dosing amount of at least about 1000 IU vitamin D, a total dosing amount of at least about 15 IU vitamin E, a total dosing amount of at least about 15 mg vitamin $B_3$, a total dosing amount of at least about 150 µg iodine, a total dosing amount of at least about 10 mg choline, a total dosing amount of at least about 15 mg iron, and a total dosing amount of at least about 75 mg omega-3 fatty acid.

In some embodiments, the methods may comprise administering at least one gummy composition to the patient, wherein the at least one gummy composition may comprise an individual dosing amount of about of vitamin A ranging from about 275 IU to about 825 IU, an individual dosing amount of vitamin $B_6$ ranging from about 0.5 mg to about 2 mg, an individual dosing amount of vitamin $B_{12}$ ranging from about 2 µg to about 8 µg, an individual dosing amount of vitamin $B_9$ ranging from about 0.25 mg to about 0.75 mg, an individual dosing amount of vitamin C ranging from about 5 mg to about 30 mg, an individual dosing amount of vitamin D from about 250 IU to about 750 IU, an individual dosing amount of vitamin E ranging from about 2.5 IU to about 7.5 IU, an individual dosing amount of vitamin $B_3$ ranging from about 3.75 mg to about 11.25 mg, an individual dosing amount of iodine ranging from about 50 µg to about 100 µg, an individual dosing amount of choline ranging from about 2 mg to about 8 mg, an individual dosing amount of iron ranging from about 0.5 mg to about 10 mg, and an individual dosing amount of at least one omega-3 fatty acid ranging from about 10 mg to about 60 mg.

In some embodiments, the methods may comprise administering at least one gummy composition to the patient, wherein the at least one gummy composition may comprise an individual dosing amount of about 367 IU vitamin A, an individual dosing amount of about 0.8 mg vitamin $B_6$, an individual dosing amount of about 2.6 µg vitamin $B_{12}$, an individual dosing amount of about 0.3 mg vitamin $B_9$, an individual dosing amount of about 10 mg vitamin C, an individual dosing amount of about 333 IU vitamin D, an individual dosing amount of about 5 IU vitamin E, an individual dosing amount of about 5 mg vitamin $B_3$, an individual dosing amount of about 50 µg iodine, an individual dosing amount of about 3.3 mg choline, an individual dosing amount of about 3.3 mg iron, and an individual dosing amount of about 25 mg of omega-3 fatty acid.

In some embodiments, the methods may comprise administering at least one gummy composition to the patient, wherein the at least one gummy composition may comprise an individual dosing amount of about 367 IU vitamin A, an individual dosing amount of about 0.8 mg vitamin $B_6$, an individual dosing amount of about 2.6 µg vitamin $B_{12}$, an individual dosing amount of about 0.3 mg vitamin $B_9$, an individual dosing amount of about 10 mg vitamin C, an individual dosing amount of about 333 IU vitamin D, an individual dosing amount of about 5 IU vitamin E, an individual dosing amount of about 5 mg vitamin $B_3$, an individual dosing amount of about 50 µg iodine, an individual dosing amount of about 3.3 mg choline, an individual dosing amount of about 4 mg iron, and an individual dosing amount of about 25 mg of omega-3 fatty acid.

In some embodiments, the methods may comprise administering at least one gummy composition to the patient, wherein the at least one gummy composition may comprise an individual dosing amount of about 367 IU vitamin A, an individual dosing amount of about 0.8 mg vitamin $B_6$, an individual dosing amount of about 2.6 µg vitamin $B_{12}$, an individual dosing amount of about 0.3 mg vitamin $B_9$, an individual dosing amount of about 10 mg vitamin C, an individual dosing amount of about 333 IU vitamin D, an individual dosing amount of about 5 IU vitamin E, an individual dosing amount of about 5 mg vitamin $B_3$, an individual dosing amount of about 50 µg iodine, an individual dosing amount of about 3.3 mg choline, an individual dosing amount of about 5 mg iron, and an individual dosing amount of about 25 mg of omega-3 fatty acid.

In some embodiments, the methods may comprise administering at least one gummy composition to the patient, wherein the at least one gummy composition may comprise an individual dosing amount of at least about 367 IU vitamin A, an individual dosing amount of at least about 0.8 mg vitamin $B_6$, an individual dosing amount of at least about 2.7

μg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 μg iodine, an individual dosing amount of at least about 3.3 mg choline, an individual dosing amount of at least about 3.3 mg iron, and an individual dosing amount of at least about 25 mg of omega-3 fatty acid.

In some embodiments, the methods may comprise administering at least one gummy composition to the patient, wherein the at least one gummy composition may comprise an individual dosing amount of at least about 367 IU vitamin A, an individual dosing amount of at least about 0.8 mg vitamin $B_6$, an individual dosing amount of at least about 2.6 μg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 μg iodine, an individual dosing amount of at least about 3.3 mg choline, an individual dosing amount of at least about 4 mg iron, and an individual dosing amount of at least about 25 mg of omega-3 fatty acid.

In some embodiments, the methods may comprise administering at least one gummy composition to the patient, wherein the at least one gummy composition may comprise an individual dosing amount of at least about 367 IU vitamin A, an individual dosing amount of at least about 0.8 mg vitamin $B_6$, an individual dosing amount of at least about 2.6 μg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 μg iodine, an individual dosing amount of at least about 3.3 mg choline, an individual dosing amount of at least about 5 mg iron, and an individual dosing amount of at least about 25 mg of omega-3 fatty acid.

Some embodiments herein provide for gummy dosage forms comprising at least one gummy composition for nutritional supplementation, wherein the at least one gummy composition may comprise vitamin A, vitamin $B_6$, vitamin $B_{12}$, vitamin $B_9$, vitamin C, vitamin D, vitamin E, vitamin $B_3$, iodine, choline, iron, and at least one omega-3 fatty acid. In some embodiments, the gummy dosage forms may comprise at least one gummy composition, wherein the at least one gummy composition may comprise a total dosing amount of about 550 IU to about 1650 IU vitamin A, a total dosing amount of about 1 mg to about 4 mg vitamin $B_6$, a total dosing amount of about 4 μg to about 12 μg vitamin $B_{12}$, a total dosing amount of about 0.5 mg to about 1.5 mg vitamin $B_9$, a total dosing amount of about 10 mg to about 40 mg vitamin C, a total dosing amount of about 500 IU to about 1500 IU vitamin D, a total dosing amount of about 7.5 IU to about 22.5 IU vitamin E, a total dosing amount of about 7 mg to about 23 mg vitamin $B_3$, a total dosing amount of about 75 μg to about 225 μg iodine, a total dosing amount of about 5 mg to about 15 mg choline, a total dosing amount of about 1 mg to about 20 mg iron, and a total dosing amount of about 50 mg to about 150 mg omega-3 fatty acid.

In some embodiments, the gummy dosage forms may comprise at least one gummy composition, wherein the at least one gummy composition may comprise a total dosing amount of about 1100 IU vitamin A, a total dosing amount of about 2.5 mg vitamin $B_6$, a total dosing amount of about 8 μg vitamin $B_{12}$, a total dosing amount of about 1 mg vitamin $B_9$, a total dosing amount of about 30 mg vitamin C, a total dosing amount of about 1000 IU vitamin D, a total dosing amount of about 15 IU vitamin E, a total dosing amount of about 15 mg vitamin $B_3$, a total dosing amount of about 150 μg iodine, a total dosing amount of about 10 mg choline, a total dosing amount of about 10 mg iron, and a total dosing amount of about 75 mg omega-3 fatty acid.

In some embodiments, the gummy dosage forms may comprise at least one gummy composition, wherein the at least one gummy composition may comprise a total dosing amount of about 1100 IU vitamin A, a total dosing amount of about 2.5 mg vitamin $B_6$, a total dosing amount of about 8 μg vitamin $B_{12}$, a total dosing amount of about 1 mg vitamin $B_9$, a total dosing amount of about 30 mg vitamin C, a total dosing amount of about 1000 IU vitamin D, a total dosing amount of about 15 IU vitamin E, a total dosing amount of about 15 mg vitamin $B_3$, a total dosing amount of about 150 μg iodine, a total dosing amount of about 10 mg choline, a total dosing amount of about 12 mg iron, and a total dosing amount of about 75 mg omega-3 fatty acid.

In some embodiments, the gummy dosage forms may comprise at least one gummy composition, wherein the at least one gummy composition may comprise a total dosing amount of about 1100 IU vitamin A, a total dosing amount of about 2.5 mg vitamin $B_6$, a total dosing amount of about 8 μg vitamin $B_{12}$, a total dosing amount of about 1 mg vitamin $B_9$, a total dosing amount of about 30 mg vitamin C, a total dosing amount of about 1000 IU vitamin D, a total dosing amount of about 15 IU vitamin E, a total dosing amount of about 15 mg vitamin $B_3$, a total dosing amount of about 150 μg iodine, a total dosing amount of about 10 mg choline, a total dosing amount of about 15 mg iron, and a total dosing amount of about 75 mg omega-3 fatty acid.

In some embodiments, the gummy dosage forms may comprise at least one gummy composition, wherein the at least one gummy composition may comprise a total dosing amount of at least about 1100 IU vitamin A, a total dosing amount of at least about 2.5 mg vitamin $B_6$, a total dosing amount of at least about 8 μg vitamin $B_{12}$, a total dosing amount of at least about 1 mg vitamin $B_9$, a total dosing amount of at least about 30 mg vitamin C, a total dosing amount of at least about 1000 IU vitamin D, a total dosing amount of at least about 15 IU vitamin E, a total dosing amount of at least about 15 mg vitamin $B_3$, a total dosing amount of at least about 150 μg iodine, a total dosing amount of at least about 10 mg choline, a total dosing amount of at least about 10 mg iron, and a total dosing amount of at least about 75 mg omega-3 fatty acid.

In some embodiments, the gummy dosage forms may comprise at least one gummy composition, wherein the at least one gummy composition may comprise a total dosing amount of at least about 1100 IU vitamin A, a total dosing amount of at least about 2.5 mg vitamin $B_6$, a total dosing amount of at least about 8 μg vitamin $B_{12}$, a total dosing amount of at least about 1 mg vitamin $B_9$, a total dosing amount of at least about 30 mg vitamin C, a total dosing amount of at least about 1000 IU vitamin D, a total dosing amount of at least about 15 IU vitamin E, a total dosing amount of at least about 15 mg vitamin $B_3$, a total dosing amount of at least about 150 μg iodine, a total dosing amount of at least about 10 mg choline, a total dosing amount of at least about 12 mg iron, and a total dosing amount of at least about 75 mg omega-3 fatty acid.

In some embodiments, the gummy dosage forms may comprise at least one gummy composition, wherein the at least one gummy composition may comprise a total dosing amount of at least about 1100 IU vitamin A, a total dosing amount of at least about 2.5 mg vitamin $B_6$, a total dosing amount of at least about 8 µg vitamin $B_{12}$, a total dosing amount of at least about 1 mg vitamin $B_9$, a total dosing amount of at least about 30 mg vitamin C, a total dosing amount of at least about 1000 IU vitamin D, a total dosing amount of at least about 15 IU vitamin E, a total dosing amount of at least about 15 mg vitamin $B_3$, a total dosing amount of at least about 150 µg iodine, a total dosing amount of at least about 10 mg choline, a total dosing amount of at least about 15 mg iron, and a total dosing amount of at least about 75 mg omega-3 fatty acid.

In some embodiments, the gummy dosage forms may comprise at least one gummy composition, wherein the at least one gummy composition may comprise an individual dosing amount of about of vitamin A ranging from about 275 IU to about 825 IU, an individual dosing amount of vitamin $B_6$ ranging from about 0.5 mg to about 2 mg, an individual dosing amount of vitamin $B_{12}$ ranging from about 2 µg to about 8 µg, an individual dosing amount of vitamin $B_9$ ranging from about 0.25 mg to about 0.75 mg, an individual dosing amount of vitamin C ranging from about 5 mg to about 30 mg, an individual dosing amount of vitamin D from about 250 IU to about 750 IU, an individual dosing amount of vitamin E ranging from about 2.5 IU to about 7.5 IU, an individual dosing amount of vitamin $B_3$ ranging from about 3.75 mg to about 11.25 mg, an individual dosing amount of iodine ranging from about 50 µg to about 100 µg, an individual dosing amount of choline ranging from about 2 mg to about 8 mg, an individual dosing amount of iron ranging from about 0.5 mg to about 10 mg, and an individual dosing amount of omega-3 fatty acid ranging from about 10 mg to about 60 mg.

In some embodiments, the gummy dosage forms may comprise at least one gummy composition, wherein the at least one gummy composition may comprise an individual dosing amount of about 367 IU vitamin A, an individual dosing amount of about 0.8 mg vitamin $B_6$, an individual dosing amount of about 2.6 µg vitamin $B_{12}$, an individual dosing amount of about 0.3 mg vitamin $B_9$, an individual dosing amount of about 10 mg vitamin C, an individual dosing amount of about 333 IU vitamin D, an individual dosing amount of about 5 IU vitamin E, an individual dosing amount of about 5 mg vitamin $B_3$, an individual dosing amount of about 50 µg iodine, an individual dosing amount of about 3.3 mg choline, an individual dosing amount of about 3.3 mg iron, and an individual dosing amount of about 25 mg of omega-3 fatty acid.

In some embodiments, the gummy dosage forms may comprise at least one gummy composition, wherein the at least one gummy composition may comprise an individual dosing amount of about 367 IU vitamin A, an individual dosing amount of about 0.8 mg vitamin $B_6$, an individual dosing amount of about 2.6 µg vitamin $B_{12}$, an individual dosing amount of about 0.3 mg vitamin $B_9$, an individual dosing amount of about 10 mg vitamin C, an individual dosing amount of about 333 IU vitamin D, an individual dosing amount of about 5 IU vitamin E, an individual dosing amount of about 5 mg vitamin $B_3$, an individual dosing amount of about 50 µg iodine, an individual dosing amount of about 3.3 mg choline, an individual dosing amount of about 4 mg iron, and an individual dosing amount of about 25 mg of omega-3 fatty acid.

In some embodiments, the gummy dosage forms may comprise at least one gummy composition, wherein the at least one gummy composition may comprise an individual dosing amount of about 367 IU vitamin A, an individual dosing amount of about 0.8 mg vitamin $B_6$, an individual dosing amount of about 2.6 µg vitamin $B_{12}$, an individual dosing amount of about 0.3 mg vitamin $B_9$, an individual dosing amount of about 10 mg vitamin C, an individual dosing amount of about 333 IU vitamin D, an individual dosing amount of about 5 IU vitamin E, an individual dosing amount of about 5 mg vitamin $B_3$, an individual dosing amount of about 50 µg iodine, an individual dosing amount of about 3.3 mg choline, an individual dosing amount of about 5 mg iron, and an individual dosing amount of about 25 mg of omega-3 fatty acid.

In some embodiments, the gummy dosage forms may comprise at least one gummy composition, wherein the at least one gummy composition may comprise an individual dosing amount of at least about 367 IU vitamin A, an individual dosing amount of at least about 0.8 mg vitamin $B_6$, an individual dosing amount of at least about 2.6 µg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 µg iodine, an individual dosing amount of at least about 3.3 mg choline, an individual dosing amount of at least about 3.3 mg iron, and an individual dosing amount of at least about 25 mg of omega-3 fatty acid.

In some embodiments, the gummy dosage forms may comprise at least one gummy composition, wherein the at least one gummy composition may comprise an individual dosing amount of at least about 367 IU vitamin A, an individual dosing amount of at least about 0.8 mg vitamin $B_6$, an individual dosing amount of at least about 2.6 µg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 µg iodine, an individual dosing amount of at least about 3.3 mg choline, an individual dosing amount of at least about 4 mg iron, and an individual dosing amount of at least about 25 mg of omega-3 fatty acid.

In some embodiments, the gummy dosage forms may comprise at least one gummy composition, wherein the at least one gummy composition may comprise an individual dosing amount of at least about 367 IU vitamin A, an individual dosing amount of at least about 0.8 mg vitamin $B_6$, an individual dosing amount of at least about 2.6 µg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 µg iodine, an individual dosing amount of at least about 3.3 mg choline, an individual dosing amount of at least about 5 mg iron, and an individual dosing amount of at least about 25 mg of omega-3 fatty acid.

Some embodiments disclosed herein relate to kits comprising the gummy dosage forms as disclosed herein. In some embodiments, the kits may comprise a gummy dosage form, wherein the gummy dosage form may comprise at least one gummy composition for nutritional supplementation, wherein the at least one gummy composition may comprise vitamin A, vitamin $B_6$, vitamin $B_{12}$, vitamin $B_9$, vitamin C, vitamin D, vitamin E, vitamin $B_3$, iodine, choline, iron, and at least one omega-3 fatty acid.

In some embodiments, the kits may comprise a gummy dosage form, wherein the gummy dosage form may comprise at least one gummy composition, wherein the at least one gummy composition may comprise an individual dosing amount of at least about 367 IU vitamin A, an individual dosing amount of at least about 0.8 mg vitamin $B_6$, an individual dosing amount of at least about 2.6 µg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 µg iodine, an individual dosing amount of at least about 3.3 mg choline, an individual dosing amount of at least about 3.3 mg iron, and an individual dosing amount of at least about 25 mg of omega-3 fatty acid.

In some embodiments, the kits may comprise a gummy dosage form, wherein the gummy dosage form may comprise at least one gummy composition, wherein the at least one gummy composition may comprise an individual dosing amount of at least about 367 IU vitamin A, an individual dosing amount of at least about 0.8 mg vitamin $B_6$, an individual dosing amount of at least about 2.6 µg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 µg iodine, an individual dosing amount of at least about 3.3 mg choline, an individual dosing amount of at least about 4 mg iron, and an individual dosing amount of at least about 25 mg of omega-3 fatty acid.

In some embodiments, the kits may comprise a gummy dosage form, wherein the gummy dosage form may comprise at least one gummy composition, wherein the at least one gummy composition may comprise an individual dosing amount of at least about 367 IU vitamin A, an individual dosing amount of at least about 0.8 mg vitamin $B_6$, an individual dosing amount of at least about 2.6 µg vitamin $B_{12}$, an individual dosing amount of at least about 0.3 mg vitamin $B_9$, an individual dosing amount of at least about 10 mg vitamin C, an individual dosing amount of at least about 333 IU vitamin D, an individual dosing amount of at least about 5 IU vitamin E, an individual dosing amount of at least about 5 mg vitamin $B_3$, an individual dosing amount of at least about 50 µg iodine, an individual dosing amount of at least about 3.3 mg choline, an individual dosing amount of at least about 5 mg iron, and an individual dosing amount of at least about 25 mg of omega-3 fatty acid.

DETAILED DESCRIPTION OF THE INVENTION

It is understood that the present invention is not limited to the particular methodologies, protocols, fillers, and excipients, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention. All references cited herein are incorporated by reference herein in their entirety.

As used herein, the term "patient" comprises any and all organisms and includes the term "subject." "Patient" may refer to a human or any other animal.

As used herein, the term "administered" or "administering" refers to the act of giving a composition to a patient or otherwise making such composition available to a patient or the patient taking a composition. The phrase "co-administration" refers to administration of two or more compositions to a patient together, which includes administration at about the same time or within a certain specific or desired time.

As used herein, the term "about," when located before a dosage amount or dosage range of a specific ingredient, refers to an amount or range closely above and/or closely below the stated amount or ranges that does not manifestly alter the therapeutic effect of the specific ingredient from the stated amount or range and is meant to encompass at least all equivalents of that amount.

Thus, when the term "about" is used before a specific value, it defines a range from the specific value minus at least 10% of the specific value to the specific value plus 10% of the specific value. For example, "about 50" defines a range from 45 or less to 55 or more. In addition, when the term "about" is used before a specific value, it may define a range from a lower limit of the specific value, the specific value minus at least 10%, the specific value minus at least 20%, the specific value minus at least 30%, the specific value minus at least 40%, the specific value minus at least 50%, the specific value minus at least 60%, the specific value minus at least 70%, the specific value minus at least 80%, and the specific value minus at least 90% to any one of the upper limit of the specific value, the specific value plus at least 10%, the specific value plus at least 20%, the specific value plus at least 30%, the specific value plus at least 40%, the specific value plus at least 50%, the specific value plus at least 60%, the specific value plus at least 70%, the specific value plus at least 80%, the specific value plus at least 90%, and the specific value plus at least 95%. It is understood that the upper limit is chosen so as to be greater than the lower limit.

As used herein, the term "dosage form" is the physical form in which the dose is to be administered to the subject or patient. The "dosage form" may include unique physical and pharmaceutical characteristics. Dosage units may be solid, liquid, or gaseous. Solid forms include pills, tablets, capsules, gel capsules, softgels, lozenges, gummies, and wafers. Such solid forms may be used as oral dosage form. In one embodiment, the dosage unit is manufactured. The manufactured dosage forms may include pills, tablets, capsules, gel capsules, softgels, gummies, lozenges and wafers. In one embodiment, the dosage form is a gummy that is homogeneous and provided in a single layer, in which all of the constituents of the gummy is provided in admixture with one another. In another embodiment, the dosage form is a gummy that comprises multiple layers each comprising a distinct group of vitamins, minerals and nutrients. The gummy compositions, in one embodiment, may have a rounded shape with no sharp edges.

As used herein, the term "gummy dosage form" refers to a dosage form of the gummy compositions disclosed herein, such as a "total dosage form" or an "individual dosage form" of the gummy compositions as used herein. Thus, a gummy dosage form may comprise a gummy composition in a total dosage form having a total dosing amount or a gummy dosage form may comprise multiple gummy compositions in individual dosage forms.

Disclosed herein are gummy dosage forms comprising gummy compositions for nutritional supplementation, methods for providing nutritional supplementation to a patient by administering gummy composition disclosed herein, and kits comprising gummy compositions for nutritional supplementation as disclosed herein. In some embodiments, the gummy compositions for nutritional supplementation may provide improved patient compliance relative to non-gummy compositions for nutritional supplementation. In certain embodiments, the gummy compositions for nutritional supplementation may comprise iron. In some embodiments, the gummy compositions may be prenatal vitamins. In some embodiments, the gummy compositions may be dietary supplements. In some embodiments, the gummy compositions may be prenatal vitamins that comprise iron.

In some embodiments, the gummy compositions for nutritional supplementation disclosed herein can be used to administer one or more vitamins, minerals, or trace elements. In some embodiments, the gummy compositions for nutritional supplementation disclosed herein may be utilized or administered for multiple indications or purposes. In one embodiment, the gummy compositions may be utilized or administered as a dietary supplement. In another embodiment, the gummy compositions may be utilized or administered as a prescription prenatal vitamin. In another embodiment, the gummy compositions may be utilized or administered to a patient. The gummy compositions may be utilized or administered to a patient in need of supplementation of any of the active ingredients contained therein. In another embodiment, the gummy compositions may be utilized or administered to a patient such as a woman during pregnancy, who is prenatal, or who is breast-feeding. In some embodiments, the gummy compositions may be utilized or administered once a day, twice a day, three times a day, four times a day, five times a day, six times a day, seven times a day, eight times a day, nine times a day, ten times a day, etc., or more, as needed.

Some embodiments provided herein relate to a method for providing nutritional supplementation to a patient, wherein the method may comprise administering at least one gummy composition to the patient. Some embodiments provided herein relate to a gummy dosage form comprising at least one gummy composition for nutritional supplementation. Some embodiments provided herein relate to a kit comprising a gummy dosage form, wherein the gummy dosage form may comprise at least one gummy composition for nutritional supplementation. The gummy compositions disclosed herein may comprise vitamin A, vitamin $B_6$, vitamin $B_{12}$, vitamin $B_9$, vitamin C, vitamin D, vitamin E, vitamin $B_3$, iodine, choline, iron, and at least one omega-3 fatty acid.

In some embodiments, a gummy composition as disclosed herein may be a "total dosage form" that comprises a "total dosing amount" of each of the active ingredients. As used herein, a "total dosing amount" means an amount or dose of an active ingredient effective to produce a desired therapeutic effect, for example, in treating a particular disease, condition, or disorder disclosed herein, or in providing nutritional supplementation. "Treating" includes producing a desired preventative, inhibitory, relieving, or ameliorative effect. The "total dosing amount" may vary, depending on the compound, the disease, the type of treatment desired and its severity, and age, weight, etc.

In some embodiments, multiple gummy compositions disclosed herein may be co-administered in methods disclosed herein to provide a total dosing amount of each of the active ingredients. The gummy dosage forms and kits disclosed herein may also comprise multiple gummy compositions that provide a total dosing amount of each of the active ingredients. In these embodiments, each gummy composition is an "individual dosage form" that comprises an "individual dosing amount" of each of the active ingredients, and the sum of the multiple individual dosing amounts approximately equals the total dosing amount. For example, one or more, two or more, three or more, four or more, five or more, six or more, seven or more, eight or more, nine or more, ten or more, etc., individual dosage forms comprising individual dosing amounts may be co-administered in the methods disclosed herein or may be included in the gummy dosage forms and kits disclosed herein to provide the total dosing amount of each of the active agents.

In some embodiments, each individual dosage form may have the same weight or may have different weight. In some embodiments, an individual dosage form may be about 50 to about 70 mg. In some embodiments, an individual dosage form may be about 70 mg to about 90 mg. In some embodiments, an individual dosage form may be about 90 mg to about 120 mg. In some embodiments, an individual dosage form may be about 120 mg to about 200 mg. In some embodiments, an individual dosage form may be about 2 g to about 5 g. In some embodiments, an individual dosage form may be about 2.5 g to about 4.5 g. In some embodiments, an individual dosage form may be about 3 g to about 3.5 g. In some embodiments, an individual dosage form may be about 50 mg, about 60 mg. about 70 mg, about 80 mg, about 90 mg, about 1 g, about 1.1 g, about 1.2 g, about 1.3 g, about 1.4 g, about 1.5 g, about 1.6 g, about 1.7 g, about 1.8 g, about 1.9 g. 2 g, about 2.1 g, about 2.2 g, about 2.3 g, about 2.4 g, about 2.5 g, about 2.6 g, about 2.7 g, about 2.8 g, about 2.9 g, about 3 g, about 3.1 g, about 3.2 g, about 3.3 g, about 3.4 g, about 3.5 g, about 3.6 g, about 3.7 g, about 3.8 g, about 3.9 g, about 4 g, about 4.1 g, about 4.2 g, about 4.3 g, about 4.4 g, about 4.5 g, about 4.6 g, about 4.7 g, about 4.8 g, about 4.9 g, or about 5 g. In some embodiments, an individual dosage form may be at least about 2 g, at least about 2.1 g, at least about 2.2 g, at least about 2.3 g, at least about 2.4 g, at least about 2.5 g, at least about 2.6 g, at least about 2.7 g, at least about 2.8 g, at least about 2.9 g, at least about 3 g, at least about 3.1 g, at least about 3.2 g, at least about 3.3 g, at least about 3.4 g, at least about 3.5 g, at least about 3.6 g, at least about 3.7 g, at least about 3.8 g, at least about 3.9 g, at least about 4 g, at least about 4.1 g, at least about 4.2 g, at least about 4.3 g, at least about 4.4 g, at least about 4.5 g, at least about 4.6 g, at least about 4.7 g, at least about 4.8 g, at least about 4.9 g, or at least about 5 g.

In some embodiments, the methods disclosed herein may comprise administering at least one gummy composition disclosed herein to a patient. In some embodiments, administering at least one gummy composition to the patient may comprise administering two of the gummy compositions disclosed herein. In some embodiments, administering at least one gummy composition to the patient may comprise administering three of the gummy compositions disclosed herein. In some embodiments, administering at least one gummy composition to the patient may comprise administering at least two of the gummy compositions disclosed herein. In some embodiments, administering at least one gummy composition to the patient may comprise administering at least three of the gummy compositions disclosed herein. In some embodiments, each individual dosage form can be administered sequentially or at about the same time.

In some embodiments, the gummy dosage forms disclosed herein may comprise at least one of the gummy compositions disclosed herein. In some embodiments, a gummy dosage form may comprise at least one gummy composition, wherein the at least one gummy composition may comprise at least two of the gummy compositions disclosed herein. In some embodiments, a gummy dosage form may comprise at least one gummy composition, wherein the at least one gummy composition may comprise at least three of the gummy compositions disclosed herein. In some embodiments, a gummy dosage form may comprise at least one gummy composition, wherein the at least one gummy composition comprises two of the gummy compositions disclosed herein. In such embodiments, a gummy dosage form may comprise at least one gummy composition, wherein the at least one gummy composition may comprise three of the gummy compositions disclosed herein.

In some embodiments, the kits disclosed herein may comprise a gummy dosage form, wherein the gummy dosage form may comprise at least one of the gummy compositions disclosed herein. In some embodiments, the kits may comprise a gummy dosage form, wherein the gummy dosage form comprises at least one gummy composition, wherein the at least one gummy composition may comprise at least two of the gummy compositions disclosed herein. In some embodiments, the kits may comprise a gummy dosage form, wherein the gummy dosage form comprises at least one gummy composition, wherein the at least one gummy composition may comprise at least three of the gummy compositions disclosed herein. In some embodiments, the kits may comprise a gummy dosage form, wherein the gummy dosage form comprises at least one gummy composition, wherein the at least one gummy composition may comprise two of the gummy compositions disclosed herein. In some embodiments, the kits may comprise a gummy dosage form, wherein the gummy dosage form comprises at least one gummy composition, wherein the at least one gummy composition may comprise three of the gummy compositions disclosed herein.

In some embodiments, gummy compositions for nutritional supplementation disclosed herein may comprise vitamin A. In some embodiments, vitamin A may be in a form that is a precursor (pro-vitamin) or metabolite of vitamin A that provides similar nutritional value as vitamin A. For example, the pro-vitamin A carotenoid may be beta carotene. Beta carotene is converted to other forms of vitamin A, specifically retinol, within the body as needed, thereby avoiding the risk of retinol toxicity. In a specific embodiment, vitamin A may be in one or more of the forms of retinol acetate (also known as retinyl acetate or vitamin A acetate), retinol (vitamin A alcohol), retinol palmitate (also known as retinyl palmitate or vitamin A palmitate), retinoic acid (tretinoin), retinal, beta-cryptoxanthin, alpha-carotene, beta-carotene, gamma-carotene, and pro-vitamin A carotenoids. In some embodiments, vitamin A may be vitamin A palmitate.

In some embodiments, a total dosing amount of vitamin A may be an amount ranging from about 1000 IU to about 2000 IU. In some embodiments, a total dosing amount of vitamin A may be an amount ranging from about 550 IU to about 1650 IU. In some embodiments, a total dosing amount of vitamin A may be an amount ranging from about 880 IU to about 1320 IU. In some embodiments, a total dosing amount of vitamin A may be an amount ranging from about 990 IU to about 1210 IU. In certain specific embodiments, a total dosing amount of vitamin A may be an amount of about 990 IU, about 1000 IU, about 1010 IU, about 1020 IU, about 1030 IU, about 1040 IU, about 1050 IU, about 1060 IU, about 1070 IU, about 1080 IU, about 1090 IU, about 1100 IU, about 1110 IU, about 1120 IU, about 1130 IU, about 1140 IU, about 1150 IU, about 1160 IU, about 1170 IU, about 1180 IU, about 1190 IU, about 1200 IU, about 1210 IU, about 1300 IU, about 1400 IU, about 1500 IU, about 1600 IU, about 1700 IU, about 1800 IU, about 1900 IU, or about 2000 IU. In certain specific embodiments, a total dosing amount of vitamin A may be an amount of at least about 990 IU, at least about 1000 IU, at least about 1010 IU, at least about 1020 IU, at least about 1030 IU, at least about 1040 IU, at least about 1050 IU, at least about 1060 IU, at least about 1070 IU, at least about 1080 IU, at least about 1090 IU, at least about 1100 IU, at least about 1110 IU, at least about 1120 IU, at least about 1130 IU, at least about 1140 IU, at least about 1150 IU, at least about 1160 IU, at least about 1170 IU, at least about 1180 IU, at least about 1190 IU, at least about 1200 IU, at least about 1210 IU, at least about 1300 IU, at least about 1400 IU, at least about 1500 IU, at least about 1600 IU, at least about 1700 IU, at least about 1800 IU, at least about 1900 IU, or at least about 2000 IU.

In some embodiments, vitamin A may be included in individual dosage forms in amounts ranging from about one-half to about one third of the total dosage amount recited above. In some embodiments, vitamin A may be included in individual dosage forms in amounts ranging from 500 IU to about 1000 IU. In some embodiments, vitamin A may be included in individual dosage forms in amounts ranging from 333 IU to about 667 IU. In some embodiments, vitamin A may be included in individual dosage forms in amounts ranging from about 275 IU to about 825 IU. In some embodiments, vitamin A may be included in individual dosage forms in amounts ranging from about 183 IU to about 550 IU. In some embodiments, vitamin A may be included in individual dosage forms in amounts ranging from about 300 IU to about 430 IU. In some embodiments, vitamin A may be included in individual dosage forms in amounts ranging from about 316 IU to about 416 IU.

In certain specific embodiments, vitamin A may be included in individual dosage forms in an amount of about 300 IU, about 305 IU, about 310 IU, about 315 IU, about 320 IU, about 325 IU, about 330 IU, about 333 IU, about 335 IU, about 340 IU, about 345 IU, about 350 IU, about 355 IU, about 340 IU, about 345 IU, about 350 IU, about 355 IU, about 360 IU, about 365 IU, about 367 IU, about 370 IU, about 375 IU, about 380 IU, about 385 IU, about 390 IU, about 395 IU, about 400 IU, about 405 IU, about 410 IU, about 415 IU, about 420 IU, about 425 IU, about 430 IU, about 435 IU, about 440 IU, about 445 IU, about 450 IU, about 455 IU, about 460 IU, about 465 IU, about 470 IU, about 475 IU, about 480 IU, about 485 IU, about 490 IU, about 495 IU, about 500 IU, about 505 IU, about 510 IU, about 515 IU, about 520 IU, about 525 IU, about 530 IU, about 535 IU, about 540 IU, about 545 IU, about 550 IU, about 555 IU, about 560 IU, about 565 IU, about 570 IU, about 575 IU, about 580 IU, about 590 IU, about 600 IU, about 605 IU, about 610 IU, about 615 IU, about 620 IU, about 625 IU, about 630 IU, about 635 IU, about 640 IU, about 645 IU, about 650 IU, about 655 IU, about 660 IU, about 665 IU, about 667 IU, about 670 IU, about 675 IU, about 680 IU, about 690 IU, about 700 IU, about 725 IU, about 750 IU, about 775 IU, about 800 IU, about 825 IU, about 850 IU, about 875 IU, about 900 IU, about 925 IU, about 950 IU, or about 975 IU, about 1000IU. In certain specific embodiments, vitamin A may be included in individual dosage forms in an amount of at least about 300 IU, at least about 305 IU, at least about 310 IU, at least about 315 IU, at least about 320 IU, at least about 325 IU, at least about 330 IU, at least about 333 IU, at least about 335 IU, at least about 340 IU, at least about 345 IU, at least about 350 IU, at least about 355 IU, at least about 340 IU, at least about 345 IU, at least about 350 IU, at least about 355 IU, at least about 360 IU, at least about 365 IU, at least about 367 IU, at least about 370 IU, at least about 375 IU, at least about 380 IU, at least about 385 IU, at least about 390 IU, at least about 395 IU, at least about 400 IU, at least about 405 IU, at least about 410 IU, at least about 415 IU, at least about 420 IU, at least about 425 IU, at least about 430 IU, at least about 435 IU, at least about 440 IU, at least about 445 IU, at least about 450 IU, at least about 455 IU, at least about 460 IU, at least about 465 IU, at least about 470 IU, at least about 475 IU, at least about 480 IU, at least about 485 IU, at least about 490 IU, at least about 495 IU, at least about 500 IU, at least about 505 IU, at least about 510 IU, at least about 515 IU, at least about 520 IU, at least about 525 IU, at least about 530 IU, at least about 535 IU, at least about 540 IU, at least about 545 IU, at least about 550 IU, at least about 555 IU, about 560 IU, at least about 565 IU, at least about 570 IU, at least about 575 IU, at least about 580 IU, at least about 590 IU, at least about 600 IU, at least about 605 IU, at least about 610 IU, at least about 615 IU, at least about 620 IU, at least about 625 IU, at least about 630 IU, at least about 635 IU, at least about 640 IU, at least about 645 IU, at least about 650 IU, at least about 655 IU, at least about 660 IU, at least about 665 IU, at least about 667 IU, at least about 670 IU, at least about 675 IU, at least about 680 IU, at least about 690 IU, at least about 700 IU, at least about 725 IU, at least about 750 IU, at least about 775 IU, at least about 800 IU, at least about 825 IU, at least about 850 IU, at least about 875 IU, at least about 900 IU, at least about 925 IU, at least about 950 IU, or at least about 975 IU, about 1000IU.

In some embodiments, vitamin A may be included in specific ranges or amounts for each specific form. When provided in their specific forms, the provided numerical range or amount includes the amounts of the specific form and/or compounds that are equivalent to the specific form. For example, vitamin A may be in the form of beta carotene and may be included in the amount of about 1100 IU. Accordingly, in this example, "beta carotene in the amount of about 1100 IU" would include 1100 IU of beta carotene and/or its equivalents and would, for example, include a product having 1100 IU retinol acetate instead of beta carotene.

In some embodiments, vitamin A may be present in an amount determined by a measure of mass, as opposed to International Units. One International Unit (IU) of vitamin A is defined as the biological equivalent of about 0.6 μg of beta carotene, or about 0.3 μg of retinol.

In some embodiments, gummy compositions for nutritional supplementation disclosed herein may comprise vitamin $B_3$. Vitamin $B_3$, or "niacin," is the common name for two compounds: nicotinic acid (also called niacin) and niacinamide (also called nicotinamide). In a specific embodiment, vitamin $B_3$ may in the forms of niacin (nicotinic acid or pyridine-3-carboxylic acid), and nicotinamide (niacinamide) and salts and esters thereof. In a specific embodiment, vitamin $B_3$ may be included in the form of niacinamide. In another specific embodiment, the present disclosure may include an equivalent molar amount of niacin.

In some embodiments, a total dosing amount of vitamin $B_3$ may be an amount ranging from about 7 mg to about 23 mg. In some embodiments, a total dosing amount of vitamin $B_3$ is an amount ranging from about 12 mg to about 18 mg. In some embodiments, a total dosing amount of vitamin $B_3$ is an amount ranging from about 13.5 mg to about 16.5 mg. In certain specific embodiments, a total dosing amount of vitamin $B_3$ is about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg. In certain specific embodiments, a total dosing amount of vitamin $B_3$ may be at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, or at least about 20 mg.

In some embodiments, vitamin $B_3$ may be included in individual dosage forms in amounts ranging from about one-half to about one third of the total dosage amount recited above. In some embodiments, vitamin $B_3$ may be included in individual dosage forms in amounts ranging from about 3.75 mg to about 11.25 mg. In some embodiments, vitamin $B_3$ may be included in individual dosage forms in amounts ranging from about 2.3 mg to about 7.7 mg. In some embodiments, vitamin $B_3$ may be included in individual dosage forms in amounts ranging from about 3 mg to about 7 mg. In certain specific embodiments, vitamin $B_3$ may be included in individual dosage forms in an amount of about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, or about 11 mg. In certain specific embodiments, vitamin $B_3$ may be included in individual dosage forms in an amount of at least about 2 mg, at least about 2.5 mg, at least about 3 mg, at least about 3.5 mg, at least about 4 mg, at least about 4.5 mg, at least about 5 mg, at least about 5.5 mg, at least about 6 mg, at least about 6.5 mg, at least about 7 mg, at least about 7.5 mg, at least about 8 mg, at least about 8.5 mg, at least about 9 mg, at least about 9.5 mg, at least about 10 mg, at least about 10.5 mg, or at least about 11 mg.

In some embodiments, vitamin $B_3$ may be included in specific ranges or amounts for each specific form. When provided in their specific forms, the provided numerical range or amount includes the amounts of the specific form and/or compounds that are equivalent to the specific form. For example, vitamin $B_3$ may be in the form of nicotinamide and may be included in the amount of about 15 mg. Accordingly, in this example, "nicotinamide in the amount of about 15 mg" would include 15 mg of nicotinamide and/or its equivalents and would, for example, include a product having 15 mg niacin instead of nicotinamide.

In some embodiments, gummy compositions for nutritional supplementation disclosed herein may comprise vitamin $B_6$. In a specific embodiment of the present invention, vitamin $B_6$ may be included in the forms of pyridoxine, 3-hydroxy-4,5-bis(hydroxymethyl)2-methylpyridine, 5'-deoxypyridoxal, 2-demethylpyridoxal(2-norpyridoxal), 2-propyl-2-norpyridoxal (2'-ethylpyridoxal), 6-methylpyridoxal, 2'-hydroxypyridoxal (2-hydroxymethyl-2-demethylpyridoxal or 2-hydroxymethyl-2-norpyridoxal), 4'-deoxypyridoxine 5'-phosphate, 5'-methylpyridoxal-5'-phosphate, pyridoxal N-oxide 5'-phosphate, Pyridoxal, Pyridoxamine, Pyridoxine-5'-phosphate (PNP), pyridoxal-5'-phosphate (PLP) and pyridoxamine-5'-phosphate (PMP), and salts and chelates thereof. In a specific embodiment, vitamin $B_6$ may be included in the form of pyridoxine hydrochloride.

In some embodiments, the total dosing amount of vitamin $B_6$ may be an amount ranging from about 1 mg to about 4 mg. In some embodiments, the total dosing amount of vitamin $B_6$ is an amount ranging from about 2 mg to about 3 mg. In some embodiments, the total dosing amount of vitamin $B_6$ is an amount ranging from about 2.3 mg to about 2.8 mg. In certain specific embodiments, the total dosing amount of vitamin $B_6$ is about 1 mg, about 1.5 mg, about 2 mg, about 2.5 mg, about 3 mg, about 3.5 mg, or about 4 mg. In certain specific embodiments, the total dosing amount of vitamin $B_6$ is at least about 1 mg, at least about 1.5 mg, at least about 2 mg, at least about 2.5 mg, at least about 3 mg, at least about 3.5 mg, or at least about 4 mg.

In some embodiments, vitamin $B_6$ may be included in individual dosage forms in amounts ranging from about one-half to about one third of the total dosage amount recited above. In some embodiments, vitamin $B_6$ may be included in individual dosage forms in amounts ranging from about 0.5 mg to about 2 mg. In some embodiments, vitamin $B_6$ may be included in individual dosage forms in amounts ranging from about 0.3 mg to about 1.3 mg. In some embodiments, vitamin $B_6$ may be included in individual dosage forms in amounts ranging from about 0.5 mg to about 1 mg. In certain specific embodiments, vitamin $B_6$ may be included in individual dosage forms in an amount of about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, or about 1.5 mg. In certain specific embodiments, vitamin $B_6$ may be included in individual dosage forms in an amount of at least about 0.5 mg, at least about 0.6 mg, at least about 0.7 mg, at least about 0.8 mg, at least about 0.9 mg, at least about 1.0 mg, at least about 1.1 mg, at least about 1.2 mg, at least about 1.3 mg, at least about 1.4 mg, or at least about 1.5 mg.

In some embodiments, vitamin $B_6$ may be included in specific ranges or amounts for each specific form. When provided in their specific forms, the provided numerical range or amount includes the amounts of the specific form and/or compounds that are equivalent to the specific form. For example, vitamin $B_6$ may be in the form of pyridoxine hydrochloride and may be included in the amount of about 2.5 mg. Accordingly, in this example, "pyridoxine hydrochloride in the amount of about 2.5 mg" would include 2.5 mg of pyridoxine hydrochloride and/or its equivalents and would, for example, include a product having 2.5 mg pyridoxamine instead of pyridoxine hydrochloride.

In some embodiments, gummy compositions for nutritional supplementation disclosed herein may comprise vitamin $B_9$. Vitamin $B_9$ is a generic name of a B-vitamin that includes multiple compounds with a general structure. For example, vitamin $B_9$ encompasses the term folate, which itself is the generic name for many different forms of this water-soluble vitamins. Indeed, folate encompasses numerous compounds that for example, are based on a pteridine ring, an aminobenzoic acid and one or more glutamic acid residues. Folic acid (pteroglutamic acid or PGA) is a synthetic form of folate, and the first folate synthesized and used as a supplement. The term folates may also be used in the generic sense to designate any members of the family of pteroylglutamates, or mixtures of them, having various levels of reduction of the pteridine ring, one-carbon substitutions and numbers of glutamate residues. Accordingly, vitamin $B_9$ is not exclusively defined by its structure, but also by its various functions, which include DNA synthesis, cell division, and as a coenzyme in one-carbon transfer reactions.

Thus, as used herein, vitamin $B_9$ may include numerous forms. In a specific embodiment, vitamin $B_9$ may be included in the form of folic acid. In some embodiments, vitamin $B_9$ may be folic acid USP (i.e. folic acid that conforms to the applicable specifications of United States Pharmacopeia ("USP")). In other embodiments, vitamin $B_9$ may be included one or more of the forms of folic acid, folacin, metafolin (also known as the calcium salt of L-5-methyl-tetrahydrofolic acid), folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof and the salts and esters thereof. In another embodiment, vitamin $B_9$ may be in the form of a folate or folate derivative thereof that is eventually converted to 5-methyl-tetrahydrofolic acid in the body and/or is absorbed into the bloodstream as 5-methyl-tetrahydrofolic acid. Folates, such as folic acid and folate, are eventually absorbed in the body and converted to L-5-methyl-tetrahydrofolic acid. In another embodiment, vitamin $B_9$ may be in the form of a folate or folate derivative thereof that increases blood folate levels, thereby reducing homocysteine levels.

In another embodiment, vitamin $B_9$ may be in the form of folate or reduced folates with various salts. In a specific embodiment, the folate and reduced folate are selected from the group consisting of D-glucosamine-folate, D-galactosamine-folate, D-glucosamine (6R, S)-tetrahydrofolate, D-glucosamine (6S)-tetrahydrofolate, D-glucosamine (6R)-tetrahydrofolate; D-galactosamine (6R, S)-tetrahydrofolate, D-galactosamine (6S)-tetrahydrofolate, D-galactosamine (6R)-tetrahydrofolate; D-glucosamine 5-methyl-(6R, S)-tetrahydrofolate, D-glucosamine 5-methyl-(6S)-tetrahydrofolate, D-glucosamine 5-methyl-(6R)-tetrahydrofolate; D-galactosamine 5-methyl-(6R, S)-tetrahydrofolate, D-galactosamine 5-methyl-(6S)-tetrahydrofolate, and D-galactosamine 5-methyl-(6R)-tetrahydrofolate. In some embodiments, vitamin $B_9$ may folic acid, a calcium salt of L-5-methyl-tetrahydrofolic acid, or a combination thereof.

In some embodiments, the total dosing amount of vitamin $B_9$ may be an amount ranging from about 0.5 mg to about 2 mg. In some embodiments, the total dosing amount of vitamin $B_9$ may be an amount ranging from about 0.5 mg to about 1.5 mg. In some embodiments, the total dosing amount of vitamin $B_9$ may be an amount ranging from about 0.8 mg to about 1.2 mg. In some embodiments, the total dosing amount of vitamin $B_9$ may be an amount ranging from about 0.9 mg to about 1.1 mg. In certain specific embodiments, the total dosing amount of vitamin $B_9$ may be about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, or about 1.5 mg. In certain specific embodiments, the total dosing amount of vitamin $B_9$ may be at least about 0.5 mg, at least about 0.6 mg, at least about 0.7 mg, at least about 0.8 mg, at least about 0.9 mg, at least about 1.0 mg, at least about 1.1 mg, at least about 1.2 mg, at least about 1.3 mg, at least about 1.4 mg, or at least about 1.5 mg.

In some embodiments, vitamin $B_9$ may be included in individual dosage forms in amounts ranging from about one-half to about one third of the total dosage amount recited above. In some embodiments, vitamin $B_9$ may be included in individual dosage forms in amounts ranging from about 0.25 mg to about 1 mg. In some embodiments, vitamin $B_9$ may be included in individual dosage forms in amounts ranging from about 0.25 mg to about 0.75 mg. In some embodiments, vitamin $B_9$ may be included in individual dosage forms in amounts ranging from about 0.3 mg to about 0.6 mg. In some embodiments, vitamin $B_9$ may be included in individual dosage forms in amounts ranging from about 0.1 mg to about 0.5 mg. In certain specific embodiments, vitamin $B_9$ may be included in individual dosage forms in an amount of about 0.1 mg, about 0.2 mg, about 0.3 mg, about 0.4 mg, about 0.5 mg, about 0.6 mg, about 0.7 mg, about 0.8 mg, about 0.9 mg, or about 1 mg. In certain specific embodiments, vitamin $B_9$ may be included in individual dosage forms in an amount of at least about 0.1 mg, at least about 0.2 mg, at least about 0.3 mg, at least about 0.4 mg, at least about 0.5 mg, at least about 0.6 mg, at least about 0.7 mg, at least about 0.8 mg, at least about 0.9 mg, or at least about 1 mg.

In some embodiments, vitamin $B_9$ may be included in specific ranges or amounts for each specific form. When provided in their specific forms, the provided numerical range or amount includes the amounts of the specific form and/or compounds that are equivalent to the specific form. For example, vitamin $B_9$ may be in the form folic acid and may be included in the amount of about 1 mg. Accordingly, in this example, "folic acid in the amount of about 1 mg" would include 1 mg of folic acid and/or its equivalents and would, for example, include a product having 1 mg 5-methyl-(6S)-tetrahydrofolic acid instead of folic acid.

In some embodiments, gummy compositions for nutritional supplementation disclosed herein may comprise vitamin $B_{12}$. Vitamin $B_{12}$ can be converted to the active coenzymes methylcobalamin and 5'-deoxyadenosylcobalamin. In certain embodiments, vitamin $B_{12}$ may be in one or more of the forms of cobalamin, methylcobalamin, 5'-deoxyadenosylcobalamin (adenosylcobalamin or cobamamide), cyanocobalamin, hydroxycobalamin and mecobalamin. In some embodiments vitamin $B_{12}$ may be cyanocobalamin.

In some embodiments, the total dosing amount of vitamin $B_{12}$ may be an amount ranging from about 4 μg to about 15 μg. In some embodiments, the total dosing amount of vitamin $B_{12}$ may be an amount ranging from about 4 μg to about 12 μg. In some embodiments, the total dosing amount of vitamin $B_{12}$ may be an amount ranging from about 6 μg to about 10 μg. In some embodiments, the total dosing amount of vitamin $B_{12}$ may be an amount ranging from about 7 μg to about 9 μg. In certain specific embodiments, the total dosing amount of vitamin $B_{12}$ may be an amount of about 4 μg, about 5 μg, about 6 μg, about 7 μg, about 8 μg, about 9 μg, about 10 μg, about 11 μg, about 12 μg, about 13 μg, about 14 μg, or about 15 μg. In certain specific embodiments, the total dosing amount of vitamin $B_{12}$ may be an amount of at least about 4 μg, at least about 5 μg, at least about 6 μg, at least about 7 μg, at least about 8 μg, at least about 9 μg, at least about 10 μg, at least about 11 μg, at least about 12 μg, at least about 13 μg, at least about 14 μg, or at least about 15 μg.

In some embodiments, vitamin $B_{12}$ may be included in individual dosage forms in amounts ranging from about one-half to about one third of the total dosage amount recited above. In some embodiments, vitamin $B_{12}$ may be included in individual dosage forms in amounts ranging from about 2 μg to about 7.5 μg. In some embodiments, vitamin B12 may be included in individual dosage forms from about 1.3 μg to about 5 μg. In some embodiments, vitamin $B_{12}$ may be included in individual dosage forms in amounts ranging from about 1.3 μg to about 8 μg. In some embodiments, vitamin $B_{12}$ may be included in individual dosage forms in amounts ranging from about 2 μg to about 8 μg. In some embodiments, vitamin $B_{12}$ may be included in individual dosage forms in amounts ranging from about 1.3 μg to about 4 μg. In some embodiments, vitamin $B_{12}$ may be included in individual dosage forms in amounts ranging from about 1.3 μg to about 3.9 μg. In some embodiments, vitamin $B_{12}$ may be included in individual dosage forms in amounts ranging from about 2 μg to about 3.2 μg. In certain specific embodiments, vitamin $B_{12}$ may be included in individual dosage forms in an amount of about 1.0 μg, about 1.1 μg, about 1.2 μg, about 1.3 μg, about 1.4 μg , about 1.5 μg, about 1.6 μg, about 1.7 μg, about 1.8 μg, about 1.9 μg, about 2 μg, about 2.1 μg, about 2.2 μg, about 2.3 μg, about 2.4 μg, about 2.5 μg, about 2.6 μg, about 2.7 μg, about 2.8 μg, about 2.9 μg, about 3.0 μg, about 3.1 μg, about 3.2 μg, about 3.3 μg, about 3.4 μg, about 3.5 μg, about 3.6 μg, about 3.7 μg, about 3.8 μg, about 3.9 μg, or about 4.0 μg. In certain specific embodiments, vitamin $B_{12}$ may be included in individual dosage forms in an amount of at least about 2 μg, at least about 2.1 μg, at least about 2.2 μg, at least about 2.3 μg, at least about 2.4 μg, at least about 2.5 μg, at least about 2.6 μg, at least about 2.7 μg, at least about 2.8 μg, at least about 2.9 μg, at least about 3.0 μg, at least about 3.1 μg, at least about 3.2 μg, at least about 3.3 μg, at least about 3.4 μg, at least about 3.5 μg, at least about 3.6 μg, at least about 3.7 μg, at least about 3.8 μg, at least about 3.9 μg, or at least about 4.0 μg, about 4.1 μg, about 4.2 μg, about 4.3 μg, about 4.4 μg, about 4.5 μg, about 4.6 μg, about 4.7 μg, about 4.8 μg, about 4.9 μg, about 5.0 μg, about 5.1 μg, about 5.2 μg, about 5.3 μg, about 5.4 μg, about 5.5 μg, about 5.6 μg, about 5.7 μg, about 5.8 μg, about 5.9 μg, about 6.0 μg, about 6.1 μg, about 6.2 μg, about 6.3 μg, about 6.4 μg, about 6.5 μg, about 6.6 μg, about 6.7 μg, about 6.8 μg, about 6.9 μg, about 7.0 μg, about 7.1 μg, about 7.2 μg, about 7.3 μg, about 7.4 μg, about 7.5 μg, about 7.6 μg, about 7.7 μg, about 7.8 μg, about 7.9 μg, or about 8.0.

In some embodiments, vitamin $B_{12}$ may be included in specific ranges or amounts for each specific form. When provided in their specific forms, the provided numerical range or amount includes the amounts of the specific form and/or compounds that are equivalent to the specific form. For example, vitamin $B_{12}$ may be in the form cyanocobalamin and may be included in the amount of about 8 μg. Accordingly, in this example, "cyanocobalamin in the amount of about 8 μg" would include about 8 μg of cyanocobalamin and/or its equivalents and would, for example, include a product having about 8 μg methylcobalamin instead of cyanocobalamin.

In some embodiments, gummy compositions for nutritional supplementation disclosed herein may comprise may comprise vitamin C. In certain embodiments, vitamin C may be included in the forms of ascorbic acid, ascorbates (calcium or sodium ascorbate), dehydroascorbic acid and salts, ascorbyl palmitate, ascorbyl phosphates and salts (such as sodium or magnesium ascorbyl phosphate), ascorbyl tetraisopalmitate, tetrahexyldecyl ascorbate, ascorbyl sulfates and salts, acylated ascorbic acid derivatives (such as 6-O-acyl-2-O-alpha-D-glucopyranosyl-L-ascorbic acids), 6-bromo-6-deoxy-L-ascorbic acid, and ascorbate salts. In a specific embodiment, vitamin C may be included in the form of ascorbic acid.

In some embodiments, the total dosing amount of vitamin C may be an amount ranging from about 5 mg to about 90 mg. In some embodiments, the total dosing amount of vitamin C may be an amount ranging from about 5 mg to about 55 mg. In some embodiments, the total dosing amount of vitamin C may be an amount ranging from about 10 mg to about 40 mg. In some embodiments, the total dosing amount of vitamin C may be an amount ranging from about 10 mg to about 50 mg. In some embodiments, the total dosing amount of vitamin C may be an amount ranging from about 20 mg to about 40 mg. In some embodiments, the total dosing amount of vitamin C may be an amount ranging from about 25 mg to about 35 mg. In certain specific embodiments, the total dosing amount of vitamin C may be an amount of about 5 mg, about 10 mg, about 15 mg, about 20 mg, about 25 mg, about 30 mg, about 35 mg, about 40 mg, about 45 mg, about 50 mg, or about 55 mg. In certain specific embodiments, the total dosing amount of vitamin C is an amount of at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, or at least about 55 mg.

In some embodiments, vitamin C may be included in individual dosage forms in amounts ranging from about one-half to about one third of the total dosage amount recited above. In some embodiments, vitamin C may be included in individual dosage forms in amounts ranging from about 2.5 mg to about 27.5 mg. In some embodiments, vitamin C may be included in individual dosage forms in amounts ranging from about 5 mg to about 30 mg. In some embodiments, vitamin C may be included in individual dosage forms in amounts ranging from about 1.6 mg to about 9.2 mg. In some embodiments, vitamin C may be included in individual dosage forms in amounts ranging from about 2 mg to about 18 mg. In some embodiments, vitamin C may be included in individual dosage forms in amounts ranging from about 5 mg to about 15 mg. In certain specific embodiments, vitamin C may be included in individual dosage forms in an amount of about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, or about 18 mg. In certain specific embodiments, vitamin C may be included in individual dosage forms in an amount of at least about 2 mg, at least about 2.5 mg, at least about 3 mg, at least about 3.5 mg, at least about 4 mg, at least about 4.5 mg, at least about 5 mg, at least about 5.5 mg, at least about 6 mg, at least about 6.5 mg, at least about 7 mg, at least about 7.5 mg, at least about 8 mg, at least about 8.5 mg, at least about 9 mg, at least about 9.5 mg, at least about 10 mg, at least about 10.5 mg, at least about 11 mg, at least about 11.5 mg, at least about 12 mg, at least about 12.5 mg, at least about 13 mg, at least about 13.5 mg, at least about 14 mg, at least about 14.5 mg, at least about 15 mg, at least about 15.5 mg, at least about 16 mg, at least about 16.5 mg, at least about 17 mg, at least about 17.5 mg, or at least about 18 mg.

In some embodiments, vitamin C may be included in specific ranges or amounts for each specific form. When provided in their specific forms, the provided numerical range or amount includes the amounts of the specific form and/or compounds that are equivalent to the specific form. For example, vitamin C may be in the form ascorbic acid and may be included in the amount of about 10 mg. Accordingly, in this example, "ascorbic acid in the amount of about 10 mg" would include 10 mg of ascorbic acid and/or its equivalents and would, for example, include a product having 10 mg ascorbyl palmitate instead of ascorbic acid.

In some embodiments, gummy compositions for nutritional supplementation disclosed herein may comprise vitamin D. In certain embodiments, vitamin D may be in one or more of the forms of vitamin $D_3$ (also known as calciol or cholecalciferol or colecalciferol), vitamin $D_2$ (also known as calciferol, ergocalciol, ergocalciferol, ercalciol, Deltalin or Viosterol), previtamin D2, ergosterol, calcitriol (also known as 1,25-dihydroxycholecalciferol), 7-dehydrocholesterol, vitamin $D_1$, vitamin $D_4$ (also known as 22-dihydroergocalciferol, 22,23-dihydroercalciol or (24S)-methylcalciol), vitamin $D_5$ (also known as (24S)-Ethylcalciol or sitocalciferol), 7-dehydrositosterol, Lumisterol, 25-hydroxyvitamin D, all steroids that exhibit the biological activity of calciol, 25-fluorocalciol, (3S)-3-amino-3-deoxycalciol, 11α-acetoxycalciol, calcidiol (also known as 25-hydroxycholecalciferol or calcifediol), ercalcitriol, calcitetrol, tacalciol (also known as tachysterol3), (5E)-isocalciol (also known as isovitamin $D_3$), Dihydroercalciol (also known as dihydrotachysterol3), (1S)-Hydroxycalciol (also known as 1α-hydroxycholecalciferol or alfacaleidol), (24R)-Hydroxycalcidiol (also known as 24(R),25-dihydroxycholecalciferol), Ercalcidiol, Ercalcitriol, Ertacalciol, (5E)-(10S)-10,19-Dihydroercalciol (also known as dihydrotachysterol 2), (6Z)-Tacalciol (also known as precalciferol or pre-vitamin D), and (22E)-(24R)-Ethyl-22,23-didehydrocalciol also known as vitamin $D_6$. In some embodiments, vitamin D may be cholecalciferol.

In some embodiments, the total dosing amount of vitamin D may be in an amount ranging from about 500 IU to about 2000 IU. In some embodiments, the total dosing amount of vitamin D may be an amount ranging from about 500 IU to about 1500 IU. In some embodiments, the total dosing amount of vitamin D may be an amount ranging from about 800 IU to about 1200 IU. In some embodiments, the total dosing amount of vitamin D may be an amount ranging from about 900 IU to about 1100 IU. In certain specific embodiments, the total dosing amount of vitamin D may be an amount of about 900 IU, about 910 IU, about 920 IU, about 930 IU, about 940 IU, about 950 IU, about 960 IU, about 970 IU, about 980 IU, about 990 IU, about 1000 IU, about 1010 IU, about 1020 IU, about 1030 IU, about 1040 IU, about 1050 IU, about 1060 IU, about 1070 IU, about 1080 IU, about 1090 IU, or about 1100 IU. In certain specific embodiments, the total dosing amount of vitamin D may be an amount of at least about 900 IU, at least about 910 IU, at least about 920 IU, at least about 930 IU, at least about 940 IU, at least about 950 IU, at least about 960 IU, at least about 970 IU, at least about 980 IU, at least about 990 IU, at least about 1000 IU, at least about 1010 IU, at least about 1020 IU, at least about 1030 IU, at least about 1040 IU, at least about 1050 IU, at least about 1060 IU, at least about 1070 IU, at least about 1080 IU, at least about 1090 IU, or at least about 1100 IU.

In some embodiments, vitamin D may be included in individual dosage forms in amounts ranging from about one-half to about one third of the total dosage amount recited above. In some embodiments, vitamin D may be included in individual dosage forms in an amount ranging from about 250 IU to about 1000 IU. In some embodiments, vitamin D may be included in individual dosage forms in an amount ranging from about 166.7 IU to about 667 IU. In some embodiments, vitamin D may be included in individual dosage forms in an amount ranging from about 250 IU to about 750 IU. In another embodiment, vitamin D may be included in individual dosage forms in an amount ranging from about 130 IU to about 540 IU. In another embodiment, vitamin D may be included in individual dosage forms in an amount ranging from about 166 IU to about 500 IU. In certain specific embodiments, vitamin D may be included in individual dosage forms in an amount of about 275 IU, about 280 IU, about 285 IU, about 290 IU, about 300 IU, about 305 IU, about 310 IU, about 315 IU, about 320 IU, about 325 IU, about 330 IU, about 333 IU, about 335 IU, about 340 IU, about 345 IU, about 350 IU, about 355 IU, about 360 IU, about 365 IU, about 370 IU, about 375 IU, about 380 IU, about 385 IU, about 390 IU, about 395 IU, about 400 IU, about 410 IU, about 420 IU, about 430 IU, about 440 IU, about 450 IU, about 460 IU, about 470 IU, about 480 IU, about 490 IU, or about 500 IU. In certain specific embodiments, vitamin D may be included in individual dosage forms in an amount of at least about 275 IU, at least about 280 IU, at least about 285 IU, at least about 290 IU, at least about 300 IU, at least about 305 IU, at least about 310 IU, at least about 315 IU, at least about 320 IU, at least about 325 IU, at least about 330 IU, at least about 333 IU, at least about 335 IU, at least about 340 IU, at least about 345 IU, at least about 350 IU, at least about 355 IU, at least about 360 IU, at least about 365 IU, at least about 370 IU, at least about 375 IU, at least about 380 IU, at least about 385 IU, at least about 390 IU, at least about 395 IU, at least about 400 IU, at least about 410 IU, at least about 420 IU, at least about 430 IU, at least about 440 IU, at least about 450 IU, at least about 460 IU, at least about 470 IU, at least about 480 IU, at least about 490 IU, or at least about 500 IU.

In some embodiments, vitamin D may be included in specific ranges or amounts for each specific form. When provided in their specific forms, the provided numerical range or amount includes the amounts of the specific form and/or compounds that are equivalent to the specific form. For example, vitamin D may be in the form vitamin $D_3$ and may be included in the amount of about 1000 IU. Accordingly, in this example, "vitamin $D_3$ in the amount of about 1000 IU" would include 1000 IU of vitamin $D_3$ and/or its equivalents and would, for example, include a product having 1000 IU vitamin $D_2$ instead of vitamin $D_3$.

In another embodiment, vitamin D may be present in an amount determined by a measure of mass, as opposed to International Units. One International Unit (IU) of vitamin D is defined as the biological equivalent of about 0.025 μg of vitamin $D_3$.

In some embodiments, gummy compositions for nutritional supplementation disclosed herein may comprise vitamin E. In some embodiments, vitamin E may be included in one or more of the forms of alpha, beta, gamma, and delta tocopherols in its natural or synthetic (dl) forms; alpha, beta, gamma, and delta tocotrienols in its natural or synthetic (dl) forms, dl-alpha tocopheryl derivatives such as dl-alpha tocopheryl esters, dl-alpha-tocopheryl acetate or succinate and d-alpha tocopheryl acetate or dl-alpha tocopheryl phosphates (such as Ester-E® manufactured by Vitamin World US®, Bohemia, N.Y.). In a specific embodiment of the present invention, vitamin E may be included in the form of d-alpha-tocopheryl acetate. In another specific embodiment, vitamin E may be included in the form of an equivalent molar amount of d-alpha tocopheryl succinate.

In some embodiments, the total dosing amount of vitamin E may be an amount ranging from about 7.5 IU to about 22.5 IU. In some embodiments, the total dosing amount of vitamin E may be an amount ranging from about 12 IU to about 18 IU. In some embodiments, the total dosing amount of vitamin E may be an amount ranging from about 13.5 IU to about 16.5 IU. In certain specific embodiments, the total dosing amount of vitamin E may be an amount of about 5 IU, about 7.5 IU, about 10 IU, about 12.5 IU, about 15 IU, about 17.5 IU, about 20 IU, or about 22.5 IU. In certain specific embodiments, the total dosing amount of vitamin E may be an amount of at least about 5 IU, at least about 7.5 IU, at least about 10 IU, at least about 12.5 IU, at least about 15 IU, at least about 17.5 IU, at least about 20 IU, or at least about 22.5 IU.

In some embodiments, vitamin E may be included in individual dosage forms in amounts ranging from about one-half to about one third of the total dosage amount recited above. In some embodiments, vitamin E may be included in individual dosage forms in amounts ranging from about 3.75 IU to about 11.25 IU. In some embodiments, vitamin E may be included in individual dosage forms in amounts ranging from about 2.5 IU to about 7.5 IU. In some embodiments, vitamin E may be included in individual dosage forms in amounts ranging from about 1 IU to about 9 IU. In some embodiments, vitamin E may be included in individual dosage forms in amounts ranging from about 4 IU to about 6 IU. In certain specific embodiments, vitamin E may be included in individual dosage forms in an amount of about 1 IU, about 1.5 IU, about 2 IU, about 2.5 IU, about 3 IU, about 3.5 IU, about 4 IU, about 4.5 IU, about 5 IU, about 5.5 IU, about 6 IU, about 6.5 IU, about 7 IU, about 7.5 IU, about 8 IU, about 8.5 IU, about 9 IU, about 9.5 IU, or about 10 IU. In certain specific embodiments, vitamin E may be included in individual dosage forms in an amount of at least about 1 IU, at least about 1.5 IU, at least about 2 IU, at least about 2.5 IU, at least about 3 IU, at least about 3.5 IU, at least about 4 IU, at least about 4.5 IU, at least about 5 IU, at least about 5.5 IU, at least about 6 IU, at least about 6.5 IU, at least about 7 IU, at least about 7.5 IU, at least about 8 IU, at least about 8.5 IU, at least about 9 IU, at least about 9.5 IU, or at least about 10 IU.

In some embodiments, vitamin E may be included in specific ranges or amounts for each specific form. When provided in their specific forms, the provided numerical range or amount includes the amounts of the specific form and/or compounds that are equivalent to the specific form. For example, vitamin E may be in the form d-alpha-tocopheryl acetate and may be included in the amount of about 7.5 IU. Accordingly, in this example, "d-alpha-tocopheryl in the amount of about 7.5 IU" would include 7.5 IU of d-alpha-tocopheryl and/or its equivalents and would, for example, include a product having 7.5 IU alpha-tocotrienol instead of d-alpha-tocopheryl.

In some embodiments, gummy compositions for nutritional supplementation disclosed herein may comprise iron. In certain embodiments, iron may be included in one or more of the forms of elemental iron, in the form of a salt, chelated form, non-chelated form, chelated to an amino acid, carbonyl iron, ferrous gluconate, ferrous fumarate, polysaccharide iron complex, elemental polysaccharide iron, polysaccharide iron, ferrous (II)-bis-glycinate chelate, ferrous asparto glycinate, ferrous bisglycinate, ferrous bisglycinate hydrochloride, ferrous bisglycinate, elemental ferrous bisglycinate, ferrous sulfate, ferronyl (micronized), as Iron Aid, iron protein succinylate, carbonyl iron, Sumalate iron, Heme iron complex, as Ferrochel amino acid chelate, heme iron polypeptide as Proferrin-bovine source, as heme iron polypeptide (bovine source), as sodium iron EDTA (Ferrazone), ferric ammonium citrate, elemental iron, ferric orthophosphate (also known as ferric phosphate or iron (III) phosphate), and ferric pyrophosphate. In a specific embodiment, iron may be included in the form of iron hydroxide polysaccharide complex. In a specific embodiment, iron may be included in the form of ferric orthophosphate. In another specific embodiment, iron may be included in the form of an equivalent molar amount of ferrous fumarate.

In some embodiments, the total dosing amount of iron may be an amount ranging from about 1 mg to about 25 mg. In some embodiments, the total dosing amount of iron may be an amount ranging from about 1 mg to about 20 mg. In some embodiments, the total dosing amount of iron may be an amount ranging from about 2 mg to about 18 mg. In some embodiments, the total dosing amount of iron may be an amount ranging from about 8 mg to about 17 mg. In some embodiments, the total dosing amount of iron may be an amount ranging from about 10 mg to about 15 mg. In some embodiments, the total dosing amount of iron is an amount ranging from about 10 mg to about 25 mg. In certain specific embodiments, the total dosing amount of iron may be an amount of about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, or about 25 mg. In certain specific embodiments, the total dosing amount of iron may be an amount of at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least 16 mg, at least about 17 mg, at least about 18 mg, at least about 19 mg, at least about 20 mg, at least about 21 mg, at least about 22 mg, at least about 23 mg, at least about 24 mg, or at least about 25 mg.

In some embodiments, iron may be included in individual dosage forms in amounts ranging from about one-half to about one third of the total dosage amount recited above. In some embodiments, iron may be included in individual dosage forms in amounts ranging from about 0.5 mg to about 10 mg. In some embodiments, iron may be included in individual dosage forms in amounts ranging from about 5 mg to about 7.5 mg. In some embodiments, iron may be included in individual dosage forms in amounts ranging from about 2 mg to about 6 mg. In some embodiments, iron may be included in individual dosage forms in amounts ranging from about 3 mg to about 5 mg. In some embodiments, iron may be included in individual dosage forms in amounts ranging from about 3.3 mg to about 5 mg.

In certain specific embodiments, iron may be included in individual dosage forms in an amount of about 3.0 mg, about 3.05 mg, about 3.1 mg, about 3.15 mg, about 3.2 mg, about 3.25 mg, about 3.3 mg, about 3.35 mg, about 3.4 mg, about 3.45 mg, about 3.5 mg, about 3.55 mg, about 3.6 mg, about 3.65 mg, about 3.7 mg, about 3.75 mg, about 3.8 mg, about 3.85 mg, about 3.9 mg, about 3.95 mg, about 4.0 mg, about 4.05 mg, about 4.1 mg, about 4.15 mg, about 4.2 mg, about 4.25 mg, about 4.3 mg, about 4.35 mg, about 4.4 mg, about 4.45 mg, about 4.5 mg, about 4.55 mg, about 4.6 mg, about 4.6 mg, about 4.7 mg, about 4.75 mg, about 4.8 mg, about 4.85 mg, about 4.9 mg, about 4.95 mg, about 5.0 mg, about 5.05 mg, about 5.1 mg, about 5.15 mg, about 5.2 mg, about 5.25 mg, about 5.3 mg, about 5.35 mg, about 5.4 mg, about 5.45 mg, about 5.5 mg, about 5.55 mg, about 5.6 mg, about 5.65 mg, about 5.7 mg, about 5.8 mg, about 5.85 mg, about 5.9 mg, about 6 mg, about 6.05 mg, about 6.1 mg, about 6.15 mg, about 6.2 mg, about 6.25 mg, about 6.3 mg, about 6.35 mg, about 6.4 mg, about 6.45 mg, about 6.5 mg, about 6.55 mg, about 6.6 mg, about 6.65 mg, about 6.7 mg, about 6.75 mg, about 6.8 mg, about 6.85 mg, about 6.9 mg, about 6.95 mg, about 7.0 mg, about 7.05 mg, about 7.1 mg, about 7.15 mg, about 7.2 mg, about 7.25 mg, about 7.3 mg, about 7.35 mg, about 7.4 mg, about 7.45 mg, about 7.5 mg, about 7.55 mg, about 7.6 mg, about 7.65 mg, about 7.7 mg, about 7.75 mg, or about 7.8 mg.

In certain specific embodiments, iron may be included in individual dosage forms in an amount of at least about 3.0 mg, at least about 3.05 mg, at least about 3.1 mg, at least about 3.15 mg, at least about 3.2 mg, at least about 3.25 mg, at least about 3.3 mg, at least about 3.35 mg, at least about 3.4 mg, at least about 3.45 mg, at least about 3.5 mg, at least about 3.55 mg, at least about 3.6 mg, at least about 3.65 mg, at least about 3.7 mg, at least about 3.75 mg, at least about 3.8 mg, at least about 3.85 mg, at least about 3.9 mg, at least about 3.95 mg, at least about 4.0 mg, at least about 4.05 mg, at least about 4.1 mg, at least about 4.15 mg, at least about 4.2 mg, at least about 4.25 mg, at least about 4.3 mg, at least about 4.35 mg, at least about 4.4 mg, at least about 4.45 mg, at least about 4.5 mg, at least about 4.55 mg, at least about 4.6 mg, at least about 4.65 mg, at least about 4.7 mg, at least about 4.75 mg, at least about 4.8 mg, at least about 4.85 mg, at least about 4.9 mg, at least about 4.95 mg, at least about 5.0 mg, at least about 5.05 mg, at least about 5.1 mg, at least about 5.15 mg, at least about 5.2 mg, at least about 5.25 mg, at least about 5.3 mg, at least about 5.35 mg, at least about 5.4 mg, at least about 5.45 mg, at least about 5.5 mg, at least about 5.55 mg, at least about 5.6 mg, at least about 5.65 mg, at least about 5.7 mg, at least about 5.8 mg, at least about 5.85 mg, at least about 5.9 mg, at least about 6 mg, at least about 6.05 mg, at least about 6.1 mg, at least about 6.15 mg, at least about 6.2 mg, at least about 6.25 mg, at least about 6.3 mg, at least about 6.35 mg, at least about 6.4 mg, at least about 6.45 mg, at least about 6.5 mg, at least about 6.55 mg, at least about 6.6 mg, at least about 6.65 mg, at least about 6.7 mg, at least about 6.75 mg, at least about 6.8 mg, at least about 6.85 mg, at least about 6.9 mg, at least about 6.95 mg, at least about 7.0 mg, at least about 7.05 mg, at least about 7.1 mg, at least about 7.15 mg, at least about 7.0 mg, at least about 7.25 mg, at least about 7.3 mg, at least about 7.35 mg, at least about 7.4 mg, at least about 7.45 mg, at least about 7.5 mg, at least about 7.55 mg, at least about 7.6 mg, at least about 7.65 mg, at least about 7.7 mg, at least about 7.75 mg, or at least about 7.8 mg.

In some embodiments, iron may be included in specific ranges or amounts for each specific form. When provided in their specific forms, the provided numerical range or amount includes the amounts of the specific form and/or compounds that are equivalent to the specific form. For example, iron may be in the form iron hydroxide polysaccharide complex and may be included in the amount to provide about 10 mg of elemental iron. Accordingly, in this example, "iron hydroxide polysaccharide complex in the amount to provide about 10 mg of elemental iron" would include the amount of iron hydroxide polysaccharide complex in the amount to provide about 10 mg of elemental iron and/or its equivalents and would, for example, include a product having ferrous fumarate instead of iron hydroxide polysaccharide complex.

In some embodiments, gummy compositions for nutritional supplementation disclosed herein may comprise iodine. In certain embodiments, iodine may be included in one or more of the forms of elemental iodine, iodized salt, Lugol's iodine, sodium iodide, potassium iodide, potassium iodate, nascent iodine, and Nano-Colloidal Detoxified Iodine. In some embodiments, iodine may be potassium iodide.

In some embodiments, the total dosing amount of iodine may be an amount ranging from about 75 μg to about 225 μg. In some embodiments, the total dosing amount of iodine may be an amount ranging from about 120 μg to about 180 μg. In some embodiments, the total dosing amount of iodine may be an amount ranging from about 135 μg to about 165 μg. In certain specific embodiments, the total dosing amount of iodine may be an amount of about 100 μg, about 110 μg, about 120 μg, about 130 μg, about 140 μg, about 150 μg, about 160 μg, about 170 μg, about 180 μg, about 190 μg, or about 200 μg. In certain specific embodiments, the total dosing amount of iodine may be an amount of at least about 100 μg, at least about 110 μg, at least about 120 μg, at least about 130 μg, at least about 140 μg, at least about 150 μg, at least about 160 μg, at least about 170 μg, at least about 180 μg, at least about 190 μg, or at least about 200 μg.

In some embodiments, iodine may be included in individual dosage forms in amounts ranging from about one-half to about one third of the total dosage amount recited above. In some embodiments, iodine may be present in individual dosage forms in amounts ranging from about 50 μg to about 100 μg. In some embodiments, iodine may be present in individual dosage forms in amounts ranging from about 37 μg to about 112 μg. In some embodiments, iodine may be present in individual dosage forms in amounts ranging from about 25 μg to about 75 μg. In some embodiments, iodine may be present in individual dosage forms in amounts ranging from about 30 μg to about 70 μg. In some embodiments, iodine may be present in individual dosage forms in amounts ranging from about 40 μg to about 60 μg. In certain specific embodiments, iodine may be present in individual dosage forms in an amount of about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, or about 100 μg. In certain specific embodiments, iodine may be present in individual dosage forms in an amount of at least about 25 μg, at least about 30 μg, at least about 35 μg, at least about 40 μg, at least about 45 μg, at least about 50 μg, at least about 55 μg, at least about 60 μg, at least about 65 μg, at least about 70 μg, at least about 75 μg, at least about 80 μg, at least about 85 μg, at least about 90 μg, at least about 95 μg, or at least about 100 μg.

In some embodiments, iodine may be included in specific ranges or amounts for each specific form. When provided in their specific forms, the provided numerical range or amount includes the amounts of the specific form and/or compounds that are equivalent to the specific form. For example, iodine may be in the form potassium iodide and may be included in the amount of about 150 μg. Accordingly, in this example, "potassium iodide in the amount of about 150 μg" would include 150 μg of potassium iodide and/or its equivalents and would, for example, include a product having 150 μg Nano-Colloidal Detoxified Iodine instead of potassium iodide.

In some embodiments, gummy compositions for nutritional supplementation disclosed herein may comprise zinc. Zinc is available in many forms and may be included in chelated or nonchelated form. In certain embodiments, zinc may be included in one or more of the forms selected from elemental zinc, zinc acetate, zinc gluconate, zinc picolinate, zinc sulfate, and zinc oxide.

In some embodiments, the total dosing amount of zinc may be an amount ranging from about 1.9 mg to about 5.7 mg. In some embodiments, the total dosing amount of zinc may be an amount ranging from about 3.0 mg to about 4.6 mg. In some embodiments, the total dosing amount of zinc may be an amount ranging from about 3.4 mg to about 4.2 mg. In certain specific embodiments, the total dosing amount of zinc may be an amount of about 3.4 mg, about 3.5 mg, about 3.6 mg, about 3.7 mg, about 3.8 mg, about 3.9 mg, about 4.0 mg, about 4.1 mg, or about 4.2 mg. In certain specific embodiments, the total dosing amount of zinc may be an amount of at least about 3.4 mg, at least about 3.5 mg, at least about 3.6 mg, at least about 3.7 mg, at least about 3.8 mg, at least about 3.9 mg, at least about 4.0 mg, at least about 4.1 mg, or at least about 4.2 mg.

In some embodiments, zinc may be included in individual dosage forms in amounts ranging from about 0.95 mg to about 2.85 mg. In some embodiments, zinc may be included in individual dosage forms in amounts ranging from about 1.3 mg to about 2.5 mg. In some embodiments, zinc may be included in individual dosage forms in amounts ranging from about 1.7 mg to about 2.1 mg. In some embodiments, zinc may be included in individual dosage forms in amounts ranging from about 1.1 mg to about 1.5 mg. In certain specific embodiments, zinc may be included in individual dosage forms in an amount of about 1.10 mg, about 1.15 mg, about 1.20 mg, about 1.25 mg, about 1.30 mg, about 1.35 mg, about 1.40 mg, about 1.45 mg, about 1.50 mg, about 1.55 mg, about 1.60 mg, about 1.65 mg, about 1.70 mg, about 1.75 mg, about 1.80 mg, about 1.85 mg, about 1.90 mg, about 1.95 mg, about 2.00 mg, about 2.05 mg, about 2.10 mg, about 2.15 mg, about 2.20 mg, about 2.25 mg, or about 2.30 mg. In certain specific embodiments, zinc may be included in individual dosage forms in an amount of at least about 1.10 mg, at least about 1.15 mg, at least about 1.20 mg, at least about 1.25 mg, at least about 1.30 mg, at least about 1.35 mg, at least about 1.40 mg, at least about 1.45 mg, at least about 1.50 mg, at least about 1.55 mg, at least about 1.60 mg, at least about 1.65 mg, at least about 1.70 mg, at least about 1.75 mg, at least about 1.80 mg, at least about 1.85 mg, at least about 1.90 mg, at least about 1.95 mg, at least about 2.00 mg, at least about 2.05 mg, at least about 2.10 mg, at least about 2.15 mg, at least about 2.20 mg, at least about 2.25 mg, or at least about 2.30 mg.

In some embodiments, zinc may be included in specific ranges or amounts for each specific form. When provided in their specific forms, the provided numerical range or amount includes the amounts of the specific form and/or compounds that are equivalent to the specific form. For example, zinc may be in the form zinc sulfate and may be included in the amount of about 1.9 mg. Accordingly, in this example, "zinc sulfate in the amount of about 1.9 mg" would include 1.9 mg of zinc sulfate and/or its equivalents and would, for example, include a product having 1.9 mg zinc oxide instead of zinc sulfate.

In some embodiments, gummy compositions for nutritional supplementation disclosed herein may comprise omega-3 fatty acids. In certain embodiments, omega-3 fatty acids may comprise one or more of docahexaenoic acid (or docosahexaenoic acid, DHA), eicosapentaenoic acid (EPA) and α-linolenic acid (ALA). In certain embodiments, omega-3 fatty acids may comprise one or more of docahexaenoic acid (or docosahexaenoic acid, DHA), eicosapentaenoic acid (EPA), or a combination thereof. In a specific embodiment, gummy compositions for nutritional supplementation disclosed herein may comprise docahexaenoic acid (or docosahexaenoic acid, DHA). In another specific embodiment, gummy compositions for nutritional supplementation disclosed herein may comprise eicosapentaenoic acid (EPA). In another specific embodiment, the gummy compositions for nutritional supplementation disclosed herein may comprise α-linolenic acid (ALA).

DHA may be obtained in solid form, such as in a whole-cell microbial product, or in liquid form, such as an oil. An example of DHA in oil form is DHASCO®-T vegetable oil from micro-algae (Martek Biosciences Corporation, Columbia, Md.). In a specific embodiment, the DHA may be DHAgold® (Martek Biosciences, Columbia, Md.), life'sDHA™ (DSM Nutritional Products, Parsippany, N.J.) (DHASCO®, Martek Biosciences Corporation, Columbia, Md.), any Algae Oil, Krill Oil and/or vegetarian DHA.

In specific embodiments, the source of DHA may be from one or more of animal, fish, plants, algae or microorganism production.

In some embodiments, gummy compositions for nutritional supplementation disclosed herein may include DHA derived from algae. In a specific embodiment, the source of DHA may be from algae oil. In other specific embodiments, the source of algae oil may be one or more of microalgae *Schizochytrium* sp., microalgae *Crypthecodinium cohnii*, microalgae *Ulkenia* sp. SAM2179, microalgae *Schizochytrium linacinum* strain SC-1. In another specific embodiment the source of DHA may be Martek Oil C53-0100 (Martek Biosciences Corporation, Columbia, Md.).

In some embodiments, the total dosing amount of omega-3 fatty acids may be an amount ranging from about 50 mg to about 500 mg. In some embodiments, the total dosing amount of omega-3 fatty acids may be an amount ranging from about 100 mg to about 500 mg. In some embodiments, the total dosing amount of omega-3 fatty acids may be an amount ranging from about 50 mg to about 475 mg. In some embodiments, the total dosing amount of omega-3 fatty acids may be an amount ranging from about 50 mg to about 150 mg. In some embodiments, the total dosing amount of omega-3 fatty acids may be an amount ranging from about 50 mg to about 100 mg. In certain specific embodiments, the total dosing amount of omega-3 fatty acids may be an amount of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, or about 250 mg. In certain specific embodiments, the total dosing amount of omega-3 fatty acids may be an amount of at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 110 mg, at least about 115 mg, at least about 120 mg, at least about 125 mg, at least about 130 mg, at least about 135 mg, at least about 140 mg, at least about 145 mg, at least about 150 mg, at least about 155 mg, at least about 160 mg, at least about 165 mg, at least about 170 mg, at least about 175 mg, at least about 180 mg, at least about 185 mg, at least about 190 mg, at least about 195 mg, at least about 200 mg, at least about 205 mg, at least about 210 mg, at least about 215 mg, at least about 220 mg, at least about 225 mg, at least about 230 mg, at least about 235 mg, at least about 240 mg, at least about 245 mg, or at least about 250 mg.

In some embodiments, omega-e fatty acids may be included in individual dosage forms in amounts ranging from about one-half to about one third of the total dosage amount recited above. In some embodiments, omega-3 fatty acids may be included in individual dosage forms in amounts ranging from about 25 mg to about 250 mg. In some embodiments, omega-3 fatty acids may be included in individual dosage forms in amounts ranging from about 16 mg to about 166 mg. In some embodiments, omega-3 fatty acids may be included in individual dosage forms in amounts ranging from about 10 mg to about 60 mg. In some embodiments, omega-3 fatty acids may be included in individual dosage forms in amounts ranging from about 15 mg to about 40 mg. In some embodiments, omega-3 fatty acids may be included in individual dosage forms in amounts ranging from about 25 mg to about 40 mg. In certain specific embodiments, omega-3 fatty acids may be included in individual dosage forms in an amount of about 5 mg. about 6 mg, about 7 mg, about 8 mg, about 9 mg, about 10 mg. about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 40 mg, about 41 mg, or about 42 mg. In certain specific embodiments, omega-3 fatty acids may be included in individual dosage forms in an amount of at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, at least about 30 mg, at least about 31 mg, at least about 32 mg, at least about 33 mg, at least about 34 mg, at least about 35 mg, at least about 36 mg, at least about 37 mg, at least about 38 mg, at least about 40 mg, at least about 41 mg, or at least about 42 mg.

In some embodiments, omega-3 fatty acids may be included in specific ranges or amounts for each specific form. When provided in their specific forms, the provided numerical range or amount includes the amounts of the specific form and/or compounds that are equivalent to the specific form. For example, omega-3 fatty acids may be in the form of DHA and may be included in the amount of about 75 mg. Accordingly, in this example, "DHA in the amount of about 75 mg" would include 75 mg of DHA and/or its equivalents and would, for example, include a product having 75 mg EPA instead of DHA.

In certain specific embodiments, DHA may be included in individual dosage forms in an amount of about 5 mg, about 10 mg, about 15 mg, about 20 mg, about 25 mg, about 30 mg, about 35 mg, about 37 mg, about 40 mg, about 45 mg, or about 50 mg. In certain specific embodiments, DHA may be included in individual dosage forms in an amount of at least about 5 mg, at least about 10 mg, at least about 15 mg, at least about 20 mg, at least about 25 mg, at least about 30 mg, at least about 35 mg, at least about 37 mg, at least about 40 mg, at least about 45 mg, or at least about 50 mg. In certain specific embodiments, EPA may be included in individual dosage forms in an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 12.5 mg, about 13 mg, about 14 mg, about 15 mg, about 16 mg, about 17 mg, about 18 mg, about 19 mg, or about 20 mg. In certain specific embodiments, EPA may be included in individual dosage forms in an amount of at least about 1 mg, at least about 2 mg, at least about 3 mg, at least about 4 mg, at least about 5 mg, at least about 6 mg, at least about 7 mg, at least about 8 mg, at least about 9 mg, at least about 10 mg, at least about 11 mg, at least about 12 mg, at least about 12.5 mg, at least about 13 mg, at least about 14 mg, at least about 15 mg, at least about 16 mg, at least about 17 mg, at least about 18 mg, at least about 19 mg, or at least about 20 mg.

In some embodiments, gummy compositions for nutritional supplementation disclosed herein may include choline. Choline (hydroxyethyl trimethyl ammonium hydroxide) is considered to be a vitamin of the B complex and is derivable from many foods. The term choline, as used herein, refers not only to the isolated choline molecule (i.e., free choline), but also to any biologically compatible salt of choline (e.g., choline bitartrate). In certain embodiments, choline may be included in one or more of the forms selected from choline bitartrate, choline chloride, choline dihydrogen citrate, choline salicylate, and choline magnesium trisalicylate. In some embodiments, choline may be choline bitartrate.

In some embodiments, the total dosing amount of choline may be an amount ranging from about 5 mg to about 15 mg. In some embodiments, the total dosing amount of choline may be an amount ranging from about 8 mg to about 12 mg. In some embodiments, the total dosing amount of choline may be an amount ranging from about 9 mg to about 11 mg. In certain specific embodiments, the total dosing amount of choline may be about 5 mg, about 6 mg, about 7 mg, about 8 mg, about 9 mg, about 10 mg, about 11 mg, about 12 mg, about 13 mg, about 14 mg, or about 15 mg. In certain specific embodiments, the total dosing amount of choline may be at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, or at least about 15 mg.

In some embodiments, choline may be included in individual dosage forms in amounts ranging from about one-half to about one third of the total dosage amount recited above. In some embodiments, choline may be included in individual dosage forms in an amount ranging from about 2 mg to about 8 mg. In some embodiments, choline may be included in individual dosage forms in an amount ranging from about 3 mg to about 7 mg. In some embodiments, choline may be included in individual dosage forms in an amount ranging from about 2.5 mg to about 4 mg. In certain specific embodiments, choline may be included in individual dosage forms in an amount of about 1.0 mg, about 1.5 mg, about 2.0 mg, about 2.5 mg, about 3 mg, about 3.1 mg, about 3.2 mg, about 3.3 mg, about 3.4 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, or about 10 mg. In certain specific embodiments, choline may be included in individual dosage forms in an amount of at least about 1.0 mg, at least about 1.5 mg, at least about 2.0 mg, at least about 2.5 mg, at least about 3 mg, at least about 3.1 mg, at least about 3.2 mg, at least about 3.3 mg, at least about 3.4 mg, at least about 3.5 mg, at least about 4.0 mg, at least about 4.5 mg, at least about 5.0 mg, at least about 5.5 mg, at least about 6.0 mg, at least about 6.5 mg, at least about 7.0 mg, at least about 7.5 mg, at least about 8.0 mg, at least about 8.5 mg, at least about 9.0 mg, at least about 9.5 mg, or at least about 10 mg.

In some embodiments, choline may be included in specific ranges or amounts for each specific form. When provided in their specific forms, the provided numerical range or amount includes the amounts of the specific form and/or compounds that are equivalent to the specific form. For example, choline may be in the form choline bitartrate and may be included in the amount of about 10 mg. Accordingly, in this example, "choline bitartrate in the amount of about 10 mg" would include 10 mg of choline bitartrate and/or its equivalents and would, for example, include a product having 10 mg choline salicylate instead of choline bitartrate.

As used herein, the terms "inactive," "inert," "excipient," and/or "formulatory" refer to any compound that is an inactive ingredient of a described composition. The definition of "inactive ingredient" as used herein follows that of the U.S. Food and Drug Administration, as defined in 21 C.F.R. 201.3(b)(8), which is any component of a drug product other than the active ingredient. By "active ingredient," then, is meant any compound intended to furnish pharmacological activity or other direct effect in the diagnosis, cure, mitigation, treatment and/or prevention of a condition. See 21 C.F.R. 210.3(b)(7). Further, "active ingredients" include those compounds of the composition that may undergo chemical change during the manufacture of the composition and be present in the final composition in a modified form intended to furnish an activity or effect. Id. These may include the vitamins, minerals, and nutrients of the gummy compositions disclosed herein. Indeed, the term "inactive ingredients" includes ingredients—such as, and only by way of example, dicalcium phosphate—that may be considered an active ingredient in another setting or composition, but that serve no therapeutic or nutritional purpose in the compositions of the present invention.

In one embodiment, the gummy composition comprises the one or more vitamins, minerals, and nutrients in combination with one or more inactive ingredients. The inactive ingredients may comprise one or more of the following: sugar, corn syrup, water, gelatin, citric acid, lactic acid, one or more glazing agents (e.g., vegetable oil, beeswax, carnauba wax), one or more natural flavors (e.g., plum, apple, mixed berry, cherry), one or more natural colors (e.g., black carrot), and one or more masking flavors (e.g., tartaric acid).

In some embodiments, the active ingredients, such as the vitamins, minerals, and nutrients of the disclosed invention, may be included in overages. Adding overages of these compounds may be necessary to meet the amounts claimed on the product label and product insert to ensure that those recited amounts are met throughout the shelf life of the product. Indeed, because of U.S. regulatory requirements that label values reflect minimum contents of these nutrients, deviations in actual nutrient content from label values are usually thought to tend toward overages. Dwyer et al., ANAL BIOANAL CHEM, 389:37-45 (2007). In some embodiments, one or more of the vitamins, minerals, and nutrients may be included in the gummy compositions of the gummy dosage forms, kits, and methods disclosed herein in overages of the recited, specific labeled amounts of about 100% to about 150% of the labeled amount, although the overages may be dependent on the stability of each ingredient. For example, overages of vitamin D and vitamin $B_{12}$ may be necessary due to the lack of stability of specific forms. In another example, 5-methyl-tetrahydrofolate, a form of vitamin $B_9$, is degraded by light, temperature and may degrade during processing and storage. Overages may be larger for some vitamins particularly those that are less stable and more likely to deteriorate with a long shelf life, those that have other functions (such as antioxidants) in the product itself; for minerals, excess amounts with larger overages are probably less likely because of their increased bulk and shelf life stability. Dwyer et al., ANAL BIOANAL CHEM, 389:37-45 (2007). Accordingly, when overages are included for any specific active ingredient, at some point in time, these ingredients with overages may degrade so that they fall within the labeled amounts. Thus, there is no literal difference between the amounts for active ingredients that include overages, and those amounts listed on the specific label. Furthermore, overages provide an equivalent efficacy of the active ingredient over the shelf life of the product. Accordingly, an active ingredient provided in overage amounts is an insubstantial change in comparison to the specific labeled amount and performs substantially the same function, in substantially the same way, and leads to substantially the same result as the same active ingredient in the labeled amount.

In one embodiment, the vitamins, minerals and nutrients may be provided in amounts that are over the amounts claimed on the labeled amount or that are over the amounts recited herein (overages). Thus, the overage amounts may be the labeled amount plus x % of the labeled amount. The overage amounts may also be the total dosing amount plus x % of the total dosing amount.

The value x may differ for each of the vitamins, minerals and nutrients depending on stability, shelf-life, and toxicity. The value for x may be about 5%, about 6%, about 7%, about 8%, about 9%, about 10%, about 15%, about 20%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%.

It is understood that the value x is determined for each of the vitamins, minerals and nutrients independently as they each have differing characteristics which may require differing overage amounts to ensure that the respective vitamins, minerals and nutrients are provided in the labeled amount for the duration of the shelf-life indicated for the gummy composition. The vitamins, minerals and nutrients have a broad range of sensitivity to temperature and light and therefore will tend to deteriorate or lose their potency at different rates.

As used herein, "labeled amount" or "labeled amounts" refer to the amount of a particular vitamin, mineral or nutrient that is claimed to be present in either a total dosing amount/forms or individual dosage amounts/forms of the gummy composition. It is understood that the labeled amounts may differ from the actual amounts of the vitamins, minerals or nutrients contained in the gummy composition by at least the overages as described above.

In one embodiment, the shelf-life is about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months about 24 months, about 25 months, about 26 months, about 27 months, about 28 months, about 29 months, about 30 months, about 31 months, about 32 months, about 33 months, about 34 months, about 35 months, about 36 months, about 4 years, about 5 years or about 6 years.

The gummy compositions for nutritional supplementation disclosed herein may comprise any necessary inactive ingredients for formulating the active ingredients in a "gummy" state. As used herein, the term "gummy" refers to a quality of the gummy compositions disclosed herein. In particular, "gummy" compositions have a degree of elasticity that is sufficient to substantially reconstitute the mass of the composition after each chew. The gummy quality results from the material not readily separating during chewing, although after continuous chewing the gummy composition will eventually break down. In certain embodiments, the gummy compositions for nutritional supplementation disclosed herein may comprise gelatin as an inactive ingredient for producing a gummy composition.

In one embodiment, the gummy composition is provided as a single layer and does not include discrete layers, such as a shell or a core having different or distinct characteristics. In accordance with this embodiment, all of the ingredients or constituents of the gummy composition are in a substantially homogeneous admixture in a gelatin form. Because the ingredients of the gummy composition are in a substantially homogeneous admixture with one another, the compatibility, stability and bioavailability of the ingredients may be affected by one another. Accordingly, in one embodiment, one or more of the ingredients may be provided in encapsulated form. In one embodiment, one or both of iron and folic acid may be provided in encapsulated forms.

Folic acid may be encapsulated prior to incorporation into the gummy composition. Folic acid may be sensitive to temperature, oxygen, light, and processing conditions. Thus in one embodiment, the folic acid may be incorporated in microcapsules using alginate and combinations of alginate and pectin polymers to improve stability in admixture with the ingredients of the gummy composition. The blended alginate and pectin polymer matrix mixtures are believed to provide an increased folic acid encapsulation efficiency and reduced leakage from the capsules as compared to hose made with alginate alone. Madziva H, et al. "Alginate-pectin microcapsules as a potential for folic acid delivery in foods." J. Microencapsul., 2005 June; 22(4):343-51. In one embodiment, the folic acid is microencapsulated with cellulose and, in particular, with ethyl cellulose to reduce degradation due to processing or manufacturing conditions. The encapsulated folic acid, therefore, comprises folic acid (folacin), ethyl cellulose and dibutyl sebecate. The folic acid may have a particle size of no less than 98% through a 40 mesh sieve and a bulk density of no more than about 0.25 g/cc. Each gram of the encapsulated folic acid delivers about 0.750 mg of folic acid. In one embodiment, the folic acid may be encapsulated in cellulose, such as a modified cellulose or an ethyl cellulose.

Similarly, iron may also be encapsulated prior to incorporation into the gummy composition in order to deliver meaningful levels of bioavailable iron without compromising taste, appearance and stability. In one embodiment, the iron may be encapsulated in cellulose, such as a modified cellulose or an ethyl cellulose.

Other ingredients that may be provided in encapsulated form, as herein described, prior to admixture with the ingredients constituting the gummy composition include those for which increased stability and prolonged shelf-life is desired. Any one or more of the following ingredients may be provided in encapsulated forms: vitamin A (as vitamin A palmitate), vitamin C (as ascorbic acid), vitamin D3 (as cholecalciferol), vitamin $B_3$ (as niacinamide), vitamin $B_6$ (as pyridoxine hydrochloride), vitamin $B_{12}$ (as cyanocobalamin), choline (as choline bitartrate), iodine (as potassium iodide), vitamin E (d-alpha tocopheryl acetate), and omega-3 Fatty Acid (as DHA).

Certain ones of the vitamins, minerals and nutrients may be provided in a matrix of starch, such as vitamin A and vitamin D3. Certain ones of the vitamins, minerals and nutrients may be provided as a hydrocolloid base.

In some embodiments, the gummy compositions may comprise one or more inactive ingredients that include but are not limited to water, buffers (including, by way of example and without limitation, phosphate buffers, citrate buffers, lactic acid, and others known to those of ordinary skill in the art), stabilizing agents (including, by way of example and without limitation, antioxidants (e.g., ascorbic acid, propionic acid, sodium bisulfite, sodium sulfite, and the like), chelating agents (e.g., fumaric acid, sodium edetate, and the like), and others known to those of ordinary skill in the art), surfactants (including, by way of example and without limitation, wetting agents (e.g. sorbitan monolaurate, etc.), antifoaming agents (e.g. sorbitan trioleate, etc.), detergents (e.g. sucrose stearate, etc.), solubilizing agents (e.g. polyethylene glycol 400 monostearate, etc.), and others known to those of ordinary skill in the art), processing aids (e.g. substances used to assist processing, including, by way of example and without limitation, lubricating agents, antioxidants, and others known to those of ordinary skill in the art), lubricating agents (including, by way of example and without limitation, stearic acid, calcium stearate, magnesium stearate, zinc stearate, talc, mineral and vegetable oils, benzoic acid, poly(ethylene glycol), glyceryl behenate, stearyl fumarate, and others known to those of ordinary skill in the art), emulsifiers (including, by way of example and without limitation, synthetic (e.g. sodium lauryl sulfate, potassium laurate, etc.), natural (e.g. gelatin, lecithin, etc.), and finely divided solid emulsifiers (e.g. bentonite, magnesium hydroxide, etc.), and others known to those of ordinary skill in the art), suspending agents (including, by way of example and without limitation, cellulose derivatives (e.g. carboxymethylcellulose, methylcellulose, ethyl cellulose, etc.), natural polymers (e.g. alginates, xanthan gum, guar gum, etc.), synthetic polymers (e.g. carbomers, polyvinyl pyrrolidone, etc.), clays (e.g. magnesium aluminum silicate, hectorite, etc.), and others known to those of ordinary skill in the art), preservatives (including, by way of example and without limitation, benzalkonium chloride, benzethonium chloride, benzyl alcohol, cetrimide, glycerin, propylene glycol, benzoic acid and sodium benzoate, potassium sorbate and sorbic acid, and others known to those of ordinary skill in the art), opaquing agents (including, by way of example and without limitation, titanium dioxide, and others known to those of ordinary skill in the art), glidants (including, by way of example and without limitation, silicon dioxide, colloidal or fumed silica, magnesium stearate, calcium stearate, stearic acid, cornstarch, talc and others known to those of ordinary skill in the art), diluents (including, by way of example and without limitation, corn syrup, lactose, sodium chloride, sucrose (sugar), and others known to those of ordinary skill in the art), colorants (including, by way of example and without limitation, FD&C Red No. 3, FD&C Red No. 20, FD&C Yellow No. 6, FD&C Blue No. 2, D&C Green No. 5, FD&C Orange No. 5, D&C Red No. 8, caramel, ferric oxide, red, pigments, dyes, tints, titanium dioxide, natural coloring agents, such as grape skin extract, beet red powder, beta carotene, annato, carmine, turneric, paprika, black carrot juice, and others known to those of ordinary skill in the art), sweeteners or sweetening agents (including, by way of example and without limitation, sucrose, fructose, fructose, high fructose corn syrup, dextrose, saccharin sodium, maltodextrin, aspartame, potassium acesulfame, neohesperidin dihydrochalcone, sucralose, monoammonium glycyrrhizinate, and others known to those of ordinary skill in the art), perfuming agents (including, by way of example and without limitation, natural flavor oil, a synthetic flavor oil, and others known to those of ordinary skill in the art), glazing agents (including, by way of example and without limitation, vegetable oil, beeswax, carnauba wax, and others known to those of ordinary skill in the art), and flavoring agents or flavorant (including, by way of example and without limitation, natural flavor oil, synthetic flavor oil, and other masking flavors known to those of ordinary skill in the art). Additional examples of other inactive ingredients are well known in the art. See, e.g., Remington: The Science and Practice of Pharmacy (21st ed. 2005).

In certain specific embodiments, gummy compositions for nutritional supplementation disclosed herein may comprise be black carrot juice. In some embodiments, a colorant may be used to mask an unappealing color, for example, that may be attributable to the presence of iron.

In certain specific embodiments, gummy compositions for nutritional supplementation disclosed herein may comprise a flavorant. In some embodiments, the flavorant may be a citrus oil, a fruit essence, an extract from a plant, an extract from a leaf, an extract from a flower, an extract from a fruit, or another masking flavor known to those of ordinary skill in the art. In some embodiments, the flavorant may be one or more of anise oil, cinnamon oil, peppermint oil, oil of wintergreen, clove oil, bay oil, anise oil, eucalyptus oil, thyme oil, cedar leave oil, oil of nutmeg, oil of sage, oil of bitter almonds, cassia oil, lemon oil, orange oil, lime oil, grapefruit oil, grape oil, apple essence, pear essence, peach essence, berry essence, wild berry essence, date essence, blueberry essence, kiwi essence, strawberry essence, raspberry essence, cherry essence, plum essence, pineapple essence, and apricot essence. Additionally, the flavorant may be one or more selected from the group consisting of citric acid, malic acid, vanilla, vanillin, cocoa, chocolate, and menthol. In some embodiments, the flavorant may include one or more of a natural plum flavor, natural apple flavor, natural mixed berry flavor, and natural cherry flavor. In some embodiments, the gummy compositions disclosed herein may comprise a masking flavor. In some embodiments, the one or more flavorants of the gummy composition may mask the taste of iron and/or DHA. It has been found that the inclusion of tartaric acid is effective in masking the undesirable flavor imparted to the composition by inclusion of iron and/or DHA. In one embodiment, the tartaric acid is provided in combination with a flavorant. In some embodiments, the one or more flavorants may increase patient compliance.

Gummy formulations may be prepared by any suitable methods. Suitable methods for preparing gummy formulations are described, for example, in U.S. Pat. Nos. 5,928, 664, 4,879,108, or 4,882,159, which are incorporated by reference in their entirety. In some embodiments, gummy formulations may be prepared by admixing an elastic, continuous glycerylated gelatin matrix with one or more active ingredients to form a homogenous mixture which is elastic, continuous and readily soluble in aqueous media. A glycerylated gelatin matrix may be prepared by heating an aqueous solution of gelatin and glycerine to a temperature and for a time sufficient to remove from about 10% to about 80% of the initial moisture content of the aqueous solution.

In one embodiment, the gelatin may be of bovine origin. Specifically, the gelatin may be produced from the partial hydrolysis of collagen contained in bovine hides and have a bloom in the range of about 260 g to about 280 g, a viscosity of greater than or equal to about 32 mp, a pH of about 4.2 to about 6.5, and a grain size of about 10 mesh.

In some embodiments, the gummy compositions disclosed herein may be packaged as kits using materials known to those of ordinary skill in the art. In some embodiments, the kit may be packaged in a sachet or package. In such embodiments, a kit may comprise one or more individual dosage forms. In some embodiments, each kit may comprise two individual dosage forms. In some embodiments, each kit may comprise three individual dosage forms. In some embodiments, a kit may comprise a total dosage form.

Another embodiment of the invention may comprise kits comprising gummy compositions packaged in blister packs. Blister packs as packaging for gummy compositions are well known to those of ordinary skill in the art. Blister packs may be made of a transparent plastic sheet which has been formed to carry a matrix of depression or blisters. One or more gummy compositions are received in each depression or blister. A foil or plastic backing is then adhered across the plane of the sheet sealing the gummy compositions in their respective blisters. Examples of materials used for the blister packs include, but are not limited to, aluminum, paper, polyester, PVC, and polypropylene. Alternative materials are known to those of ordinary skill in the art. To remove a gummy composition, the depression material is pressed in and the composition is pushed through the backing material. Multiple blister packs may be placed in an outer package, often a box or carton for sale and distribution.

Another specific embodiment of the present disclosure may comprise gummy compositions packaged in bottles. The bottle may be glass or plastic in form with a pop or screw top cap. Bottle packaging for compositions in gummy form are well known to those of ordinary skill in the art. In some embodiments, the bottle may comprise multiple packages having multiple individual dosage forms.

Additionally, an individual dosage form or total dosage form may be individually wrapped, packaged as multiple units on paper strips or in vials of any size, without limitation. The gummy compositions of the invention may be packaged in unit dose, rolls, bulk bottles, blister packs and combinations thereof, without limitation.

In some embodiments, any vitamins, nutrients and/or minerals may be explicitly excluded from the gummy compositions disclosed herein. By way of non-limiting example, in some embodiments, the gummy compositions disclosed herein may be substantially free of added alpha carotene; substantially free of added lutein; substantially free of added lycopene; substantially free of added zeaxanthin; substantially free of added vitamin $B_4$; substantially free of added vitamin $B_5$; substantially free of added vitamin $B_7$; substantially free of added vitamin $B_8$; substantially free of added vitamin $B_{10}$; substantially free of added vitamin $B_{11}$; substantially free of added calcium; substantially free of added chromium; substantially free of added copper; substantially free of added manganese; substantially free of added selenium; substantially free of added boron; substantially free of added odorless garlic; substantially free of added coenzyme Q-10; substantially free of added 1-carnitine; substantially free of added grape seed extract; substantially free of added green tea extract; substantially free of added quercetin; substantially free of added hawthorne berries; and/or substantially free of added alpha lipoic acid. In some embodiments, the gummy compositions may be substantially free of other added vitamins and minerals.

The term "substantially free of added" as used herein means free from therapeutically effective amounts of compounds when administered in suggested doses, but may include trace amounts of compounds in non-therapeutically effective amounts. For example, a composition of the present disclosure that includes an inactive ingredient that is a salt or compound including a mineral would still be substantially free of added minerals. For example, trace amounts of titanium dioxide may be provided. Titanium dioxide which is an effective opacifier in powder form, where it is employed as a pigment to provide whiteness and opacity to numerous pharmaceutical products.

The present disclosure will be further illustrated by the following non-limiting Examples. These Examples are understood to be exemplary only, and they are not to be construed as limiting the scope of the invention as defined by the appended embodiments.

EXAMPLES

Example 1

A Representative Individual Dosage Form (For Co-Administration of Two Individual Dosage Forms)

| INGREDIENT | AMOUNT |
| --- | --- |
| Vitamin A (as retinol acetate) | 550 IU |
| Vitamin $B_6$ (as pyridoxine hydrochloride) | 1.25 mg |
| Vitamin $B_{12}$ (as cyanocobalamin) | 4 µg |
| Vitamin $B_9$ (as folic acid) | 0.5 mg |
| Vitamin C (as ascorbic acid) | 15 mg |
| Vitamin D (as cholecalciferol) | 500 IU |
| Vitamin E (as DL-alpha-tocopheryl acetate) | 7.5 IU |
| Vitamin $B_3$ (as niacinamide) | 7.5 mg |
| Zinc (as zinc sulphate) | 1.9 mg |
| Iodine (as potassium iodide) | 75 µg |
| Choline (as choline bitartrate) | 5 mg |
| Elemental Iron (as iron hydroxide polysaccharide complex) | 4 mg |
| Omega-3 Fatty Acids (includes 25 mg DHA and 5 mg EPA) | 35 mg |

Inactive Ingredients: Corn Syrup, Sugar, Gelatin, Lactic Acid, Natural Flavors, Black Carrot Juice.

Example 2

A Representative Individual Dosage Form (For Co-Administration of Three Individual Dosage Forms)

| INGREDIENT | AMOUNT |
| --- | --- |
| Vitamin A (as retinol acetate) | 367 IU |
| Vitamin $B_6$ (as pyridoxine hydrochloride) | 0.83 mg |
| Vitamin $B_{12}$ (as cyanocobalamin) | 2.67 µg |
| Vitamin $B_9$ (as folic acid) | 0.33 mg |
| Vitamin C (as ascorbic acid) | 6.67 mg |
| Vitamin D (as cholecalciferol) | 333 IU |
| Vitamin E (as DL-alpha-tocopheryl acetate) | 5 IU |

-continued

| INGREDIENT | AMOUNT |
|---|---|
| Vitamin $B_3$ (as niacinamide) | 5 mg |
| Zinc (as zinc sulphate) | 1.27 mg |
| Iodine (as potassium iodide) | 50 µg |
| Choline (as choline bitartrate) | 3.33 mg |
| Elemental Iron (as iron hydroxide polysaccharide complex) | 4 mg |
| Omega-3 Fatty Acids (includes 25 mg DHA and 5 mg EPA) | 35 mg |

Inactive Ingredients: Corn Syrup, Sugar, Gelatin, Lactic Acid, Natural Flavors, Black Carrot Juice.

Example 3

A Representative Individual Dosage Form (For Co-Administration of Three Individual Dosage Forms)

| INGREDIENT | AMOUNT |
|---|---|
| Vitamin A (as vitamin A palmitate) | 367 IU |
| Vitamin $B_6$ (as pyridoxine hydrochloride) | 0.83 mg |
| Vitamin $B_{12}$ (as cyanocobalamin) | 2.7 µg |
| Vitamin $B_9$ (as folic acid USP and the calcium salt of L-5-methyl-tetrahydrofolic acid in a ratio of 2:3, respectively) | 0.33 mg |
| Vitamin C (as ascorbic acid) | 10 mg |
| Vitamin D (as cholecalciferol) | 333.33 IU |
| Vitamin E (as d-alpha-tocopheryl acetate) | 5 IU |
| Vitamin $B_3$ (as niacinamide) | 5 mg |
| Iodine (as potassium iodide) | 0.05 mg |
| Choline (as choline bitartrate) | 3.33 mg |
| Iron (as ferric orthophosphate) | 3.33 mg |
| Omega-3 Fatty Acid (as DHA) | 25 mg |

Inactive Ingredients: Sugar, Corn Syrup, Water, Gelatin, Citric Acid, Lactic Acid, Vegetable Oil, Beeswax, Carnauba Wax, Natural Flavors, Black Carrot Juice, Masking Flavor.

Example 4

A Representative Individual Dosage Form (For Co-Administration of Three Individual Dosage Forms)

| INGREDIENT | AMOUNT |
|---|---|
| Vitamin A (as vitamin A palmitate) | 367 IU |
| Vitamin $B_6$ (as pyridoxine hydrochloride) | 0.83 mg |
| Vitamin $B_{12}$ (as cyanocobalamin) | 2.7 µg |
| Vitamin $B_9$ (as folic acid USP and the calcium salt of L-5-methyl-tetrahydrofolic acid in a ratio of 2:3, respectively) | 0.33 mg |
| Vitamin C (as ascorbic acid) | 10 mg |
| Vitamin D (as cholecalciferol) | 333.33 IU |
| Vitamin E (as d-alpha-tocopheryl acetate) | 5 IU |
| Vitamin $B_3$ (as niacinamide) | 5 mg |
| Iodine (as potassium iodide) | 0.05 mg |
| Choline (as choline bitartrate) | 3.33 mg |
| Iron (as ferric orthophosphate) | 4 mg |
| Omega-3 Fatty Acid (as DHA) | 25 mg |

Inactive Ingredients: Sugar, Corn Syrup, Water, Gelatin, Citric Acid, Lactic Acid, Vegetable Oil, Beeswax, Carnauba Wax, Natural Flavors, Black Carrot Juice, Masking Flavor.

Example 5

A Representative Individual Dosage Form (For Co-Administration of Three Individual Dosage Forms)

| INGREDIENT | AMOUNT |
|---|---|
| Vitamin A (as vitamin A palmitate) | 367 IU |
| Vitamin $B_6$ (as pyridoxine hydrochloride) | 0.83 mg |
| Vitamin $B_{12}$ (as cyanocobalamin) | 2.7 µg |
| Vitamin $B_9$ (as folic acid USP and the calcium salt of L-5-methyl-tetrahydrofolic acid in a ratio of 2:3, respectively) | 0.33 mg |
| Vitamin C (as ascorbic acid) | 10 mg |
| Vitamin D (as cholecalciferol) | 333.33 IU |
| Vitamin E (as d-alpha-tocopheryl acetate) | 5 IU |
| Vitamin $B_3$ (as niacinamide) | 5 mg |
| Iodine (as potassium iodide) | 0.05 mg |
| Choline (as choline bitartrate) | 3.33 mg |
| Iron (as ferric orthophosphate) | 5 mg |
| Omega-3 Fatty Acid (as DHA) | 25 mg |

Inactive Ingredients: Sugar, Corn Syrup, Water, Gelatin, Citric Acid, Lactic Acid, Vegetable Oil, Beeswax, Carnauba Wax, Natural Flavors, Black Carrot Juice, Masking Flavor.

Example 6

A Representative Individual Dosage Form (For Co-Administration of a Single Individual Dosage Forms)

The amounts below reflect the amounts of an individual dosage form.

| INGREDIENT | LABELED AMOUNT | ANALYTICAL MINIMUM | OVERAGE RANGE |
|---|---|---|---|
| Vitamin A (as vitamin A palmitate) | 1100 IU | 1705 IU | ±45% to +60% |
| Vitamin C (as ascorbic acid) | 30 mg | 54 mg | ±80% to +95% |
| Vitamin D3 (as cholecalciferol) | 1000 IU | 1550 IU | ±25% to +60% |
| Vitamin $B_3$ (as niacinamide) | 15 mg | 19.50 mg | ±25% to +40% |
| Vitamin $B_6$ (as pyridoxine hydrochloride) | 2.5 mg | 3.25 mg | ±25% to +40% |
| Vitamin $B_{12}$ (as cyanocobalamin) | 8 µg | 10.64 µg | ±33% to +40% |
| Choline (as choline bitartrate) | 10 mg | 11.00 mg | ±10% to +20% |
| Iodine (as potassium iodide) | 150 µg | 195 µg | ±10% to +40% |
| Iron (as ferric orthophosphate) | 10 mg | 10.60 mg | ±6% to +10% |
| Vitamin $B_9$ (encapsulated folic acid) | 1000 µg | 1750 µg | ±75% to +85% |
| Vitamin E (d-alpha tocopheryl acetate) | 15 IU | 18 IU | ±20% to +30% |
| Omega-3 Fatty Acid (as DHA) | 75 mg | 87 mg | ±16% to +32% |

Inactive Ingredients: sugar, corn syrup, water, gelatin, citric acid, lactic acid, glazing agent (vegetable oil, beeswax, carnauba wax), natural flavors (plum, apple, mixed berries, cherry), natural colors (black carrot), and masking flavors (tartaric acid).

Example 7

A Representative Individual Dosage Form (For Co-Administration of Two Individual Dosage Forms)

The amounts below reflect the amounts of an individual dosage form.

| INGREDIENT | LABELED AMOUNT | ANALYTICAL MINIMUM | OVERAGE |
|---|---|---|---|
| Vitamin A (as vitamin A palmitate) | 550 IU | 852.5 IU | ±45% to +60% |
| Vitamin C (as ascorbic acid) | 15 mg | 27 mg | ±80% to +95% |
| Vitamin D3 (as cholecalciferol) | 500 IU | 775 IU | ±25% to +60% |
| Vitamin $B_3$ (as niacinamide) | 7.5 mg | 9.75 mg | ±25% to +40% |
| Vitamin $B_6$ (as pyridoxine hydrochloride) | 1.25 mg | 1.08 mg | ±25% to +40% |
| Vitamin $B_{12}$ (as cyanocobalamin) | 4 µg | 5.32 µg | ±33% to +40% |
| Choline (as choline bitartrate) | 5 mg | 5.5 mg | ±10% to +20% |
| Iodine (as potassium iodide) | 75 µg | 97.5 µg | ±10% to +40% |
| Iron (as ferric orthophosphate) | 5 mg | 5.3 mg | ±6% to +10% |
| Vitamin $B_9$ (encapsulated folic acid) | 500 µg | 875 µg | ±75% to +85% |
| Vitamin E (d-alpha tocopheryl acetate) | 7.5 IU | 9 IU | ±20% to +30% |
| Omega-3 Fatty Acid (as DHA) | 37.5 mg | 43.5 mg | ±16% to +32% |

Inactive Ingredients: sugar, corn syrup, water, gelatin, citric acid, lactic acid, glazing agent (vegetable oil, beeswax, carnauba wax), natural flavors (plum, apple, mixed berries, cherry), natural colors (black carrot), and masking flavors (tartaric acid).

Example 8

A Representative Individual Dosage Form (For Co-Administration of Three Individual Dosage Forms Packaged Together in a Sachet)

The amounts below reflect the amounts of an individual dosage form.

| INGREDIENT | LABELED AMOUNT | ANALYTICAL MINIMUM | OVERAGE |
|---|---|---|---|
| Vitamin A (as vitamin A palmitate) | 367 IU | 568.33 IU | ±45% to +60% |
| Vitamin C (as ascorbic acid) | 10 mg | 18 mg | ±80% to +95% |
| Vitamin D3 (as cholecalciferol) | 333 IU | 516.67 IU | ±25% to +60% |
| Vitamin $B_3$ (as niacinamide) | 5 mg | 6.5 mg | ±25% to +40% |
| Vitamin $B_6$ (as pyridoxine hydrochloride) | 0.83 mg | 1.08 mg | ±25% to +40% |
| Vitamin $B_{12}$ (as cyanocobalamin) | 2.67 µg | 3.55 µg | ±33% to +40% |
| Choline (as choline bitartrate) | 3.33 mg | 3.67 mg | ±10% to +20% |
| Iodine (as potassium iodide) | 50 µg | 65 µg | ±10% to +40% |
| Iron (as ferric orthophosphate) | 3.33 mg | 3.53 mg | ±6% to +10% |
| Vitamin $B_9$ (encapsulated folic acid) | 333 µg | 583.33 µg | ±75% to +85% |
| Vitamin E (d-alpha tocopheryl acetate) | 5 IU | 6 IU | ±20% to +30% |
| Omega-3 Fatty Acid (as DHA) | 25 mg | 29 mg | ±16% to +32% |

Inactive Ingredients: sugar, corn syrup, water, gelatin, citric acid, lactic acid, glazing agent (vegetable oil, beeswax, carnauba wax), natural flavors (plum, apple, mixed berries, cherry), natural colors (black carrot), and masking flavors (tartaric acid).

Example 9

Clinical Trial Conducted with Representative Gummy Compositions

A study is undertaken to evaluate the effectiveness of the gummy compositions disclosed herein for the treatment of patients. The objective of the study is to determine whether oral intake of the gummy compositions results in an improvement of the nutritional status of patients with regard to the specific vitamins and minerals contained in the administered compositions, particularly through improved patient compliance.

A double-blind, placebo controlled study is conducted over a six-month period. A total of 120 subjects (60 pregnant women entering the second trimester of pregnancy and 60 lactating women), aged 20-35 years, are chosen for the study. An initial assessment of the nutritional status of each woman is conducted. Vitamin A and vitamin $B_6$ are measured using high performance liquid chromatography. Vitamin $B_3$ levels are assessed by measuring urinary excretion of N'methylnicotinamide and its pyridone. Vitamin $B_9$ is measured by radioimmunoassay (RIA), specifically The Solid Phase No Biol Folic Acid Kit (Diagnostic Products, Los Angeles, Calif.). Vitamin $B_{12}$ is measured by RIA using human intrinsic factor as a binder. Vitamin C levels are measured by spectrophotometric and colorimetric methods. Vitamin D is measured using an extraction double-antibody RIA (Dia Sorin, Inc., Stillwater, Minn.). The peroxide hemolysis test is used to determine vitamin E status. Iron levels are measured using standard spectrophotometry. Iodine levels are measured by HPLC. Zinc levels are assessed using flame atomic absorption spectrometry (Perkins Elmer 460, Norwalk, Conn.). DHA is measured and quantified using gas chromatography procedures.

Additionally, total serum homocysteine levels are determined by extraction on the Multi-Prep® gravity series GVSA-100 column, a strong anion exchange gravity flow column, and measurement by gas chromatography/mass spectrometry. Biochemical Diagnostics, Austin, Tex.

The 120 subjects are separated into four separate groups of 30 women. In a first group comprising only pregnant women and in a second group comprising only lactating women, each subject is administered two individual dosage forms of the gummy compositions as described in Example 1 once a day. In a third group comprising only pregnant women and in a fourth group comprising only lactating women, each subject is administered two placebo dosage forms once a day. Thus, dosage form administration occurs every 24 hours. No other nutritional supplements are taken by the subjects during the assessment period.

An assessment of the nutritional status of each woman is conducted utilizing the methods described above at one month intervals for a six month period. The data is evaluated using multiple linear regression analysis and a standard t-test. In each analysis, the baseline value of the outcome variable is included in the model as a covariant. Treatment by covariant interaction effects is tested by standard methods. If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 1, 2, 3, 4, 5, and 6 months, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

An unexpected statistically significant improvement in the nutritional status of vitamin, mineral, and nutrient levels measured is observed in the treated subjects over the controls upon completion of the study. Of note, homocysteine levels in women receiving supplements remain unelevated. Moreover, patients in the test group show high patient compliance and do not report significant adverse events. Therefore, the study confirms that oral administration of the compositions disclosed herein are effective in improving the nutritional status of patients. Other unexpected results relate to the observation that the length of gestation is increased by approximately six days in women receiving supplements due to DHA intake, and their homocysteine levels are not elevated due to folic acid intake, leading to a better prognosis regarding risk of neural tube defects in their infants.

What is claimed:

1. A method for treating a prenatal, pregnant or breastfeeding patient for a disease, condition or disorder that is associated with a nutritional deficiency in the patient, the method comprising:
   administering one or more gummy compositions to a patient, wherein the one or more gummy compositions consists of:
   a total dosing amount of about 1000 IU to about 2000 IU of vitamin A,
   a total dosing amount of about 1 mg to about 4 mg of vitamin B6,
   a total dosing amount of about 4 µg to about 15 µg of vitamin B12,
   a total dosing amount of about 0.5 mg to about 2.0 mg of encapsulated vitamin B9,
   a total dosing amount of about 5 mg to about 90 mg of vitamin C,
   a total dosing amount of about 500 IU to about 2000 IU of vitamin D,
   a total dosing amount of about 7.5 IU to about 22.5 IU of vitamin E,
   a total dosing amount of about 7 mg to about 23 mg of vitamin B3,
   a total dosing amount of about 75 µg to about 225 µg of iodine,
   a total dosing amount of about 5 mg to about 15 mg of choline,
   a total dosing amount of about 1 mg to about 25 mg of encapsulated iron,
   a total dosing amount of about 50 mg to about 500 mg of at least one omega-3 fatty acid, water, and
   one or more inactive ingredients selected from the group consisting of: sucrose, glucose, syrup, gelatin, lactic acid, citric acid, flavorants, colorants, and propylene glycol
   to treat a disease, condition or disorder in the patient that is associated with a nutritional deficiency in the patient;
   wherein the vitamins, minerals and omega-3 fatty acids in each of the one or more gummy compositions is provided in a single homogenous layer which is elastic and continuous.

2. The method of claim 1, further comprising:
   administering two to four individual gummy compositions to a patient, wherein each individual gummy composition consists of:
   an individual dosing amount of vitamin A ranging from about 275 IU to about 825 IU,
   an individual dosing amount of vitamin B6 ranging from about 0.5 mg to about 2 mg,
   an individual dosing amount of vitamin B12 ranging from about 2 µg to about 8 µg,
   an individual dosing amount of encapsulated vitamin B9 ranging from about 0.25 mg to about 0.75 mg,
   an individual dosing amount of vitamin C ranging from about 5 mg to about 30 mg,
   an individual dosing amount of vitamin D from about 250 IU to about 750 IU,
   an individual dosing amount of vitamin E ranging from about 2.5 IU to about 7.5 IU,
   an individual dosing amount of vitamin B3 ranging from about 3.75 mg to about 11.25 mg,
   an individual dosing amount of iodine ranging from about 50 to about 100 µg,
   an individual dosing amount of choline ranging from about 2 mg to about 8 mg,
   an individual dosing amount of encapsulated iron ranging from about 0.5 mg to about 10 mg, and
   an individual dosing amount of at least one omega-3 fatty acid ranging from about 10 mg to about 60 mg.

3. The method of claim 1, further comprising:
   administering three to four individual gummy compositions to a patient, wherein each individual gummy composition consists of:
   an individual dosing amount of about 367 IU vitamin A,
   an individual dosing amount of about 0.8 mg vitamin B6,
   an individual dosing amount of about 2.6 µg vitamin B12,
   an individual dosing amount of about 0.3 mg encapsulated vitamin B9,
   an individual dosing amount of about 10 mg vitamin C,
   an individual dosing amount of about 333 IU vitamin D,
   an individual dosing amount of about 5 IU vitamin E,
   an individual dosing amount of about 5 mg vitamin B3,
   an individual dosing amount of about 50 µg iodine,
   an individual dosing amount of about 3.3 mg choline,
   an individual dosing amount of about 3.3 mg encapsulated iron, and
   an individual dosing amount of about 25 mg of at least one omega-3 fatty acid.

4. The method of claim 1, further comprising:
administering three to four individual gummy compositions to a patient, wherein each individual gummy composition consists of:
an individual dosing amount of about 367 IU vitamin A,
an individual dosing amount of about 0.8 mg vitamin B6,
an individual dosing amount of about 2.6 µg vitamin B12,
an individual dosing amount of about 0.3 mg encapsulated vitamin B9,
an individual dosing amount of about 10 mg vitamin C,
an individual dosing amount of about 333 IU vitamin D,
an individual dosing amount of about 5 IU vitamin E,
an individual dosing amount of about 5 mg vitamin B3,
an individual dosing amount of about 50 µg iodine,
an individual dosing amount of about 3.3 mg choline,
an individual dosing amount of about 4 mg encapsulated iron, and
an individual dosing amount of about 25 mg of at least one omega-3 fatty acid.

5. The method of claim 1, further comprising:
administering three to four individual gummy compositions to a patient, wherein each individual gummy composition consists of:
an individual dosing amount of about 367 IU vitamin A,
an individual dosing amount of about 0.8 mg vitamin B6,
an individual dosing amount of about 2.6 µg vitamin B12,
an individual dosing amount of about 0.3 mg encapsulated vitamin B9,
an individual dosing amount of about 10 mg vitamin C,
an individual dosing amount of about 333 IU vitamin D,
an individual dosing amount of about 5 IU vitamin E,
an individual dosing amount of about 5 mg vitamin B3,
an individual dosing amount of about 50 µg iodine,
an individual dosing amount of about 3.3 mg choline,
an individual dosing amount of about 5 mg encapsulated iron, and
an individual dosing amount of about 25 mg of at least one omega-3 fatty acid.

6. A composition for treating a prenatal, pregnant or breastfeeding patient for a disease, condition or disorder that is associated with a nutritional deficiency in the patient, the composition comprising:
one or more gummy compositions, wherein the one or more gummy compositions consists of:
a total dosing amount of about 1000 IU to about 2000 IU of vitamin A,
a total dosing amount of about 1 mg to about 4 mg of vitamin B6,
a total dosing amount of about 4 µg to about 15 µg of vitamin B12,
a total dosing amount of about 0.5 mg to about 2.0 mg of encapsulated vitamin B9,
a total dosing amount of about 5 mg to about 90 mg of vitamin C,
a total dosing amount of about 500 IU to about 2000 IU of vitamin D,
a total dosing amount of about 7.5 IU to about 22.5 IU of vitamin E,
a total dosing amount of about 7 mg to about 23 mg of vitamin B3,
a total dosing amount of about 75 µg to about 225 µg of iodine,
a total dosing amount of about 5 mg to about 15 mg of choline,
a total dosing amount of about 1 mg to about 25 mg of encapsulated iron,
a total dosing amount of about 50 mg to about 500 mg of at least one omega-3 fatty acid, water, and
one or more inactive ingredients selected from the group consisting of: sucrose, glucose, syrup, gelatin, lactic acid, citric acid, flavorants, colorants, and propylene glycol
to treat a disease, condition or disorder in the patient that is associated with a nutritional deficiency in the patient; and
wherein the vitamins, minerals and omega-3 fatty acids in each of the one or more gummy compositions is provided in a single homogenous layer which is elastic and continuous.

7. The composition of claim 6, further comprising:
administering two to four individual gummy compositions to a patient, wherein each individual gummy composition consists of:
an individual dosing amount of vitamin A ranging from about 275 IU to about 825 IU,
an individual dosing amount of vitamin B6 ranging from about 0.5 mg to about 2 mg,
an individual dosing amount of vitamin B12 ranging from about 2 µg to about 8 µg,
an individual dosing amount of encapsulated vitamin B9 ranging from about 0.25 mg to about 0.75 mg,
an individual dosing amount of vitamin C ranging from about 5 mg to about 30 mg,
an individual dosing amount of vitamin D from about 250 IU to about 750 IU,
an individual dosing amount of vitamin E ranging from about 2.5 IU to about 7.5 IU,
an individual dosing amount of vitamin B3 ranging from about 3.75 mg to about 11.25 mg,
an individual dosing amount of iodine ranging from about 50 µg to about 100 µg,
an individual dosing amount of choline ranging from about 2 mg to about 8 mg,
an individual dosing amount of encapsulated iron ranging from about 0.5 mg to about 10 mg, and
an individual dosing amount of at least one omega-3 fatty acid ranging from about 10 mg to about 60 mg.

8. The composition of claim 6, further comprising:
administering three to four individual gummy compositions to a patient, wherein each individual gummy composition consists of:
an individual dosing amount of about 367 IU vitamin A,
an individual dosing amount of about 0.8 mg vitamin B6,
an individual dosing amount of about 2.6 µg vitamin B12,
an individual dosing amount of about 0.3 mg encapsulated vitamin B9,
an individual dosing amount of about 10 mg vitamin C,
an individual dosing amount of about 333 IU vitamin D,
an individual dosing amount of about 5 IU vitamin E,
an individual dosing amount of about 5 mg vitamin B3,
an individual dosing amount of about 50 µg iodine,
an individual dosing amount of about 3.3 mg choline,
an individual dosing amount of about 3.3 mg encapsulated iron, and
an individual dosing amount of about 25 mg of at least one omega-3 fatty acid.

9. The composition of claim 6, further comprising:
administering three to four individual gummy compositions to a patient, wherein each individual gummy composition consists of:
an individual dosing amount of about 367 IU vitamin A,
an individual dosing amount of about 0.8 mg vitamin B6,
an individual dosing amount of about 2.6 µg vitamin B12, an individual dosing amount of about 0.3 mg encapsulated vitamin B9,
an individual dosing amount of about 10 mg vitamin C,
an individual dosing amount of about 333 IU vitamin D,
an individual dosing amount of about 5 IU vitamin E,
an individual dosing amount of about 5 mg vitamin B3,
an individual dosing amount of about 50 µg iodine,
an individual dosing amount of about 3.3 mg choline,
an individual dosing amount of about 4 mg encapsulated iron, and
an individual dosing amount of about 25 mg of at least one omega-3 fatty acid.

10. The composition of claim 6, further comprising:
administering three to four individual gummy compositions to a patient, wherein each individual gummy composition consists of:
an individual dosing amount of about 367 IU vitamin A,
an individual dosing amount of about 0.8 mg vitamin B6,
an individual dosing amount of about 2.6 µg vitamin B12,
an individual dosing amount of about 0.3 mg encapsulated vitamin B9,
an individual dosing amount of about 10 mg vitamin C,
an individual dosing amount of about 333 IU vitamin D,
an individual dosing amount of about 5 IU vitamin E,
an individual dosing amount of about 5 mg vitamin B3,
an individual dosing amount of about 50 µg iodine,
an individual dosing amount of about 3.3 mg choline,
an individual dosing amount of about 5 mg encapsulated iron, and
an individual dosing amount of about 25 mg of at least one omega-3 fatty acid.

11. The method of claim 1, wherein the one or more gummy compositions is a prenatal vitamin or dietary supplement.

12. The method of claim 1, wherein the one or more gummy compositions has improved patient compliance relative to a non-gummy composition comprising the same vitamins, minerals and omega-3 fatty acid.

13. The method of claim 1, wherein the patient is a pregnant woman, prenatal woman, or a woman who is breast-feeding.

14. The composition of claim 6, wherein the one or more gummy compositions is a prenatal vitamin or dietary supplement.

15. The composition of claim 6, wherein the one or more gummy compositions has improved patient compliance relative to a non-gummy composition comprising the same vitamins, minerals and omega-3 fatty acid.

16. The composition of claim 6, wherein the patient is a pregnant woman, prenatal woman, or a woman who is breast-feeding.

17. The composition of claim 6, wherein the single homogenous layer does not include a shell.

* * * * *